(12) United States Patent
Wangh

(10) Patent No.: US 7,915,014 B2
(45) Date of Patent: Mar. 29, 2011

(54) SPECIALIZED OLIGONUCLEOTIDES AND THEIR USE IN NUCLEIC ACID AMPLIFICATION AND DETECTION

(75) Inventor: Lawrence J. Wangh, Auburndale, MA (US)

(73) Assignee: Brandeis University, Waltham, WA (US)

( * ) Notice: Subject to any disclaimer, the term of this patent is extended or adjusted under 35 U.S.C. 154(b) by 330 days.

(21) Appl. No.: 11/826,683

(22) Filed: Jul. 17, 2007

(65) Prior Publication Data

US 2008/0193934 A1 Aug. 14, 2008

Related U.S. Application Data

(60) Provisional application No. 60/831,223, filed on Jul. 17, 2006.

(51) Int. Cl.
*C12P 19/34* (2006.01)
(52) U.S. Cl. ...................................... 435/91.2
(58) Field of Classification Search ................. None
See application file for complete search history.

(56) References Cited

U.S. PATENT DOCUMENTS

| 2004/0072182 A1 | 4/2004 | Lyamichev et al. |
| 2004/0106109 A1 | 6/2004 | Belly et al. |
| 2004/0219570 A1 | 11/2004 | Salerno |

FOREIGN PATENT DOCUMENTS

WO    WO-01/94638 A2    12/2001

OTHER PUBLICATIONS

Pierce et al. Real-time PCR using molecular beacons for accurate detection of the Y chromosome in single human blastomeres. Hum. Mol. Reprod. 6:1155-64 (2000).*
Tyagi et al. Molecular Beacons:Probes that fluoresce upon hybridization. Nature Biotechnology 14:303-308 (1996).*
Heid et al. Real Time Quantitative PCR. Genome Research 6:986-94 (1996).*
Lyamichev et al. Polymorphism identification and quantitative detection of genomic DNA by invasive cleavage of oligonucleotide probes. Nature Biotechnology 17:292-6 (1999).*
New England Biolabs: Description of Taq Polymerase [online] [retrieved Jun. 9, 2010] retrieved from http://www.neb.com/nebecomm/productsM0273.asp.*
K. E. Pierce et al., "Detection of cystic fibrosis alleles from single cells using molecular beacons and a novel method of asymmetric real-time PCR," Molecular Human Reproduction, vol. 9, No. 12, 2003, pp. 815-820.
K. E. Pierce et al., "Linear-After-The-Exponential (LATE)-PCR: Primer design criteria for high yields of specific single-stranded DNA and improved real-time detection," Proc. Natl. Acad. Sci. USA, vol. 102, No. 34, Jun. 14, 2005, pp. 8609-8614.
J. A. Sanchez et al., "Linear-After-The-Exponential (LATE)-PCR: An advanced method of asymmetric PCR and its uses in quantitative real-time analysis," Proc. Natl. Acad. Sci. USA, vol. 101, No. 7, Feb. 17, 2004, pp. 1933-1938.
International Search Report (7 pgs.).
Written Opinion (5 pgs.).
Kenneth E. Pierce, et al., "Detection of cystic fibrosis alleles from single cells using molecular beacons and a novel method of asymmetric real-time PCR", Molecular Human Reproduction, Oxford University Press, GB-BE, vol. 9, No. 12, Dec. 1, 2003; pp. 815-820, XP002397152; ISSN: 1360-9947; Abstract, p. 816, column 1—column 2; figure 1.
J.A. Sanchez, et al., "Linear-after-the-exponential (LATE)-PCR: an advanced method of asymmetric PCR and its uses in quantitative real-time analysis" Proceedings of the National Academy of Sciences of USA, National Academy of Science, Washington, D.C., US, vol. 101, No. 7, Feb. 17, 2004; pp. 1933-1938, XP002990854; ISSN: 0027-8424; Abstract.
Extended European Search Report Communication issued Jan. 4, 2010, in European Application No. 07796898.0-2403.
Communication pursuant to Article 94(3) EPC in EP Appln No: 07 796 898.0 dated Nov. 17, 2010.

* cited by examiner

*Primary Examiner* — Samuel C Woolwine
(74) *Attorney, Agent, or Firm* — Foley & Lardner LLP

(57) ABSTRACT

Described herein are labeled probes and unlabeled oligonucleotides that are useful for use in nucleic acid amplification reactions. These probes and oligonucleotides are modified to alter their sensitivity to primer-independent 5' exonuclease activity of a thermostable DNA polymerase relative to its corresponding unmodified counterpart. Non-symmetric polymerase chain reaction (PCR) amplification and detection methods employing these labeled probes and unlabeled oligonucleotides are also described. Kits for nucleic acid amplification reactions including labeled probes and unlabeled oligonucleotides are also described.

11 Claims, 13 Drawing Sheets

Fig. 6
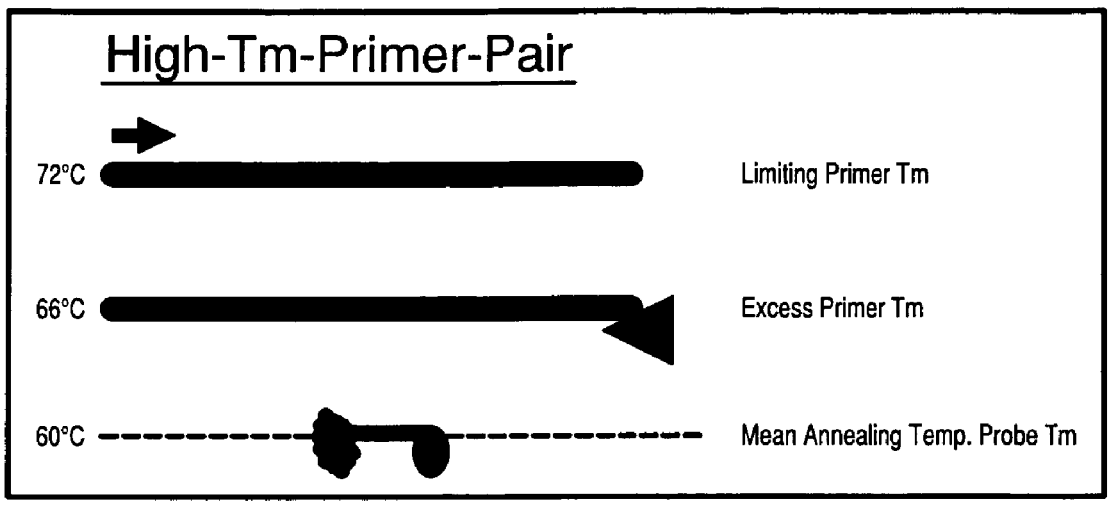
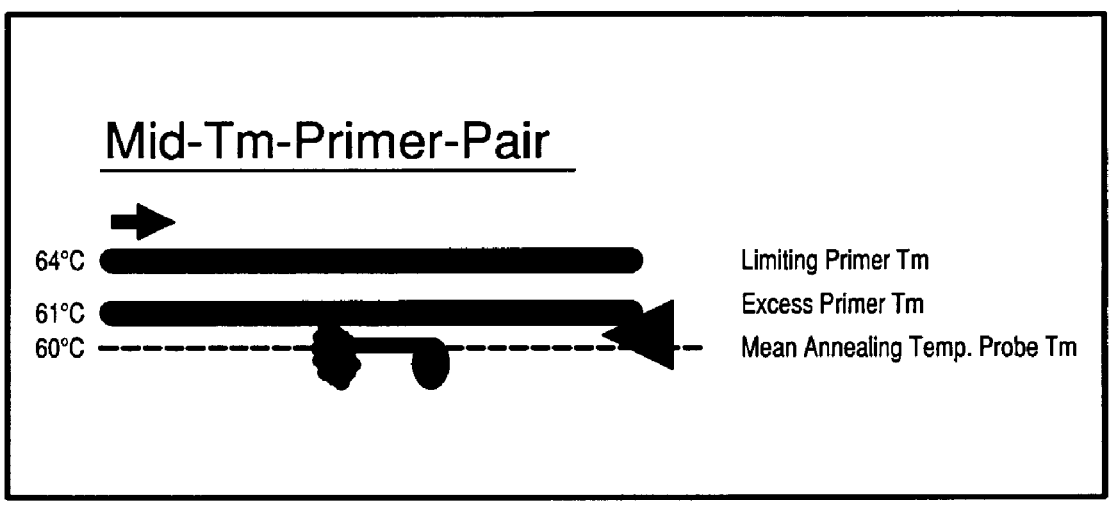
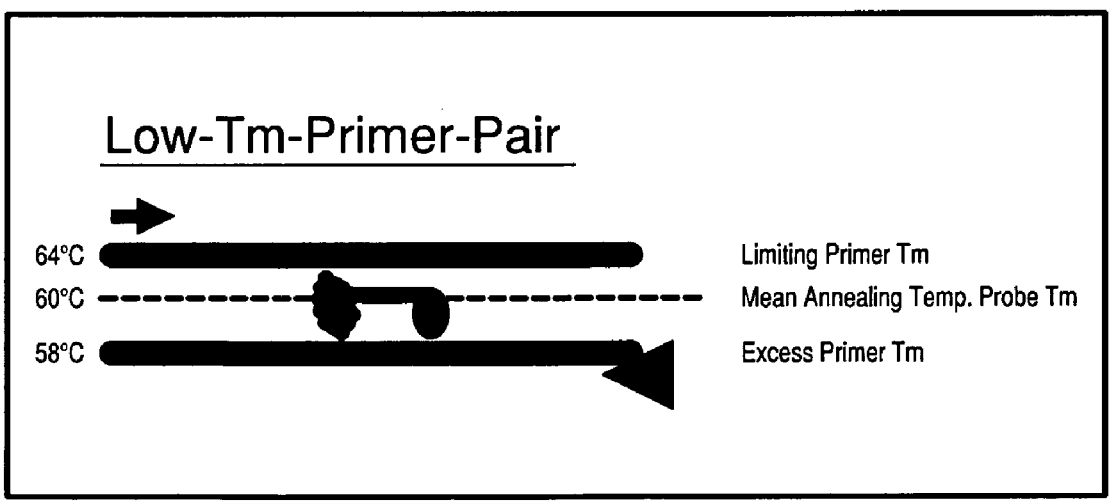

SPECIALIZED OLIGONUCLEOTIDES AND THEIR USE IN NUCLEIC ACID AMPLIFICATION AND DETECTION

CROSS-REFERENCE TO RELATED PATENT APPLICATIONS

This application claims priority to and the benefit of U.S. provisional application No. 60/831,223, filed Jul. 17, 2006, hereby incorporated by reference in its entirety.

SEQUENCE LISTING

The instant application contains a Sequence Listing which has been submitted via EFS-Web and is hereby incorporated by reference in its entirety. Said ASCII copy, created on Aug. 9, 2010, is named 03850382.txt and is 9,448 bytes in size.

TECHNICAL FIELD

This application relates to nucleic acid amplification reactions and detection of amplified products, including particularly amplifications utilizing the polymerase chain reaction, commonly known as PCR.

BACKGROUND OF THE INVENTION

Nucleic acid amplification techniques and assays are well known. Some reactions for amplifying DNA are isothermal, such as nucleic acid sequence base amplification (NASBA). Others employ thermal cycling, such as the polymerase chain reaction (PCR). Amplification and assays employing amplification utilizing PCR are described, for example, in U.S. Pat. Nos. 4,683,202, 4,683,195, and 4,965,188, and, generally, PCR PROTOCOLS, a guide to Methods and Applications, INNIS et al. eds., Academic Press (San Diego, Calif. (USA) 1990), each of which is hereby incorporated by reference in its entirety. PCR amplifications are generally designed to be symmetric, that is, to make double-stranded products (or "amplicons") by utilizing equimolar or approximately equimolar concentrations of a pair of matched primers, that is, a forward primer and a reverse primer that have equal melting temperatures (Tm's). A technique that has found limited use for making largely single-stranded amplicons directly in a PCR amplification reaction is "asymmetric PCR," described in Gyllensten and Erlich, "Generation of Single-Stranded DNA by the Polymerase Chain Reaction and Its Application to Direct Sequencing of the HLA-DQA Locus," Proc. Natl. Acad. Sci. (USA) 85: 7652-7656 (1988); and U.S. Pat. No. 5,066,584. Asymmetric PCR is a non-symmetric PCR amplification method that differs from symmetric PCR in that one of the primers is diluted fivefold to one hundredfold so as to be present in limiting amount of 1-20 percent of the concentration of thee other primer. As a consequence, the amplification consists of an exponential phase in which both primers are extended, generating double-stranded amplicon, followed by linear amplification in which only one primer remains, generating single-stranded amplicon.

A more recent non-symmetric PCR amplification method is "Linear-After-The-Exponential PCR" LATE-PCR), which utilizes primers in different concentrations but wherein the primers are not "matched" as in symmetric PCR and asymmetric PCR. Sanchez et al. (2004) Proc. Natl. Acad. Sci. (USA) 101:1933-1938, published international patent application WO 03/054233 (3 Jul. 2003), and Pierce et al. (2005) Proc. Natl. Acad. Sci. (USA) 102; 8609-8614, all of which are incorporated herein by reference in their entirety. DNA amplification methods can be used for RNA targets by first performing reverse transcription to create cDNA, which is then amplified, for example, by one of the foregoing PCR methods.

Detection and analysis of nucleic acid amplification products can be performed in a variety of ways. Double-stranded amplicons can be monitored with a dye that fluoresces upon intercalating into or otherwise interacting with double-stranded DNA, such and SYBR Green or SYBR Gold. See, for example, U.S. Pat. No. 5,994,056. Amplicons can be subjected to a sequencing reaction, for example, conventional dideoxy sequencing or Pyrosequencing, a real-time sequencing-by-synthesis method. Hybridization probes are commonly used for detection. Probes may be labeled or unlabeled. Detection of hybridized probes may be by a physical characteristic, such as size, by participation in a subsequent event, for example, a color-forming reaction, or by detection of a label applied to the probe, such as a radioactive or fluorescent label. Examples of labeled probes are 5' Nuclease probes that are cleaved during primer extension (U.S. Pat. Nos. 5,210,015, 5,487,972 and 5,538,848), molecular beacon probes (U.S. Pat. Nos. 5,925,517, 6,103,476 and 6,365,729), Yin-Yang double-stranded probes (Li, Q. et al (2002) Nucl. Acids Res. 30:e5) and FRET probe pairs.

All of the above PCR based methods of amplification depend on the action of a thermostable DNA polymerase recovered from bacterial source. In their native form these enzymes are single polypeptides with several domains and several activities: including a 5' to 3' polymerase, a 5' to 3' exonuclease, and a 3' to 5' editing function (which is deleted from commercially used enzymes). Taq DNA polymerase (from *Thermus aquaticus*) is the most widely used, including hot-start forms, but Tfi DNA Polymerase (Invitrogen, Inc, product #30342-011) is another such enzyme. In addition to these thermostable DNA polymerases there are several thermostable DNA polymerases which also carry out reverse transcription of RNA into DNA, along with polymerization of DNA strands and exonuclease cleavage of certain 5' ends. These enzymes include ZO5 polymerase and *Thermus thermophilus* (TTH) polymerase.

The 5' to 3' exonuclease activity found in the thermostable DNA polymerases has been much studied using Taq polymerase. For instance, this exonuclease activity is the basis of so-called 5' nuclease assays used in connection with symmetric PCR. The 5' nuclease assays utilize two primers and a probe. The probe is a linear, or random coil, DNA oligonucleotide having a fluorophore covalently linked to one terminal nucleotide and a nonfluorescent quencher covalently linked to the other terminal nucleotide. It hybridizes to one of the two target strands to which one of the two primers binds. The melting temperature of a 5' nuclease probe is higher than that of its upstream primer, and the probe is therefore located downstream of the extending primer. The 5' to 3' exonuclease activity of the Taq polymerase encounters and cleaves the 5' end of the probe as the 5' to 3' polymerase domain of the enzyme extends the 3' end of the primer. If the probe has a fluorescent moiety on its 5' end, that moiety and the nucleotide to which it is covalently linked are separated from the rest of the oligomer by cleavage. If the remainder of the oligonucleotide is still bound to the target sequence, it is cleaved again by the 5' exonuclease of the advancing polymerase. This is primer-dependent cleavage of the probe.

Primer-dependent cleavage of the probe has the following characteristics: 1) The 3' end of the primer must have an unblocked (or uncapped) 3' —OH group. Thus, addition of —PO₄ or other chemical moiety to the 3' —OH, or removal of the 3' OH, prevents cleavage. 2) The primer must advance up to and/or "invade under" the 5' end of the probe. Thus, except as noted below, omission of one or more nucleotide triphosphates from a primer-dependent reaction will prevent cleavage, if the primer cannot advance up to the 5' end of the probe. The exception to this rule is that a primer with a 3' OH can be designed which already invades under the 5' end of the probe without additional extension. 3) If the 3' end of the primer that already invades under the 5' end of the probe, that 3' end must be complementary to the target sequence. Thus, a non-complementary 3' extension (arm) of 2 or more nucleotides at the 3' end of the primer prevents primer dependent cleavage of the probe, even if the 3' —OH is uncapped. Removal of the 5' to 3' domain of Taq polymerase generates an enzyme known as the Stoffel fragment. PCR amplifications utilizing the Stoffel fragment cannot use 5' nuclease (TAQMAN, a trademark of Roche Molecular Systems)) probes. Construction of probes, such as molecular beacons, using certain modified nucleotides, such as 2' o-methyl nucleotides across their entire length prevent primer-dependent cleavage the probe.

Lyamichev et al. (Biochemistry (2000) 39: 9523-9532) described an invasive signal amplification reaction based on the three oligonucleotide structural features characteristic of primer-dependent cleavage of a probe. They reported that "by running the reaction at an elevated temperature, the downstream oligonucleotide cycles on and off the target leading to multiple cleavage events per target molecule without temperature cycling".

The 5' to 3' exonuclease activity of thermostable DNA polymerases is also known to carry out primer-independent cleavage of a probe-target hybrid. This reaction has been studied using hairpin-shaped target molecules with stems of 16 base-pairs, loops of 4 nucleotides, and 5' ends that are labeled with $P^{32}$—$PO_4$. The two arms of the hairpin are either equally long (i.e. it is blunt ended), or the 3' arm extends beyond the 5' end, or the 5' end extends beyond the 3' end. Using molecules of this design the primer-independent 5' to 3' exonuclease activity of Taq Polymerase has been shown to have the following characteristics: 1) Lyamichev, V., et al. (Science 260, 778-783 (1993)) reported that in the absence of a primer the 5' to 3' nuclease of Taq polymerase cleaved the recessed 5' end of a hairpin substrate between the last two base pairs of the substrate strand and the target strand. 2) Lyamichev et al. (Proc. National Acad. Sci. 96: 6143-6148 (1999)) demonstrated that the 5' to 3' exonuclease activity of intact Taq polymerase (TaqNP) does not efficiently cleave the 5' end of a hairpin structure whose 3' end was recessed by 6 nucleotides. These authors concluded that "low efficiency of cleavage probably results from binding of the polymerase domain of this enzyme to the end of the duplex, which resembles a template-primer complex". They did not test subtrates that resemble probes hybridized to targets rather than primers hybridized to targets.

For certain amplification objectives and for certain detection objectives, the amplification methods and the detection methods known in the art are unsuitable or have limitations. For example, multiplexed PCR assays can only distinguish among five or six targets by differently colored fluorescent probes. Also, it is very difficult to detect a rare allele in a sample containing an abundant allele.

SUMMARY OF THE INVENTION

An aspect of this invention is non-symmetric PCR methods that include signal amplification using a low-temperature linear DNA hybridization probe that is modified to render it sensitive to primer-independent 5' exonuclease activity of a thermostable DNA polymerase relative to its corresponding unmodified counterpart.

Another aspect of this invention is non-symmetric PCR methods that include detection of hybridization of a low-temperature linear DNA hybridization probe that is modified to render it resistant to primer-independent 5' exonuclease activity of a thermostable DNA polymerase.

Another aspect of this invention is PCR methods in which amplification of one target or allele is selectively blocked.

BRIEF DESCRIPTION OF THE DRAWINGS

FIG. 6 A schematic illustrating the relationship of the EXO-R probe and the various primer pairs utilized in Example 3 and FIG. 7.

DETAILED DESCRIPTION OF THE PREFERRED EMBODIMENTS

A. Definitions

Figure 1:
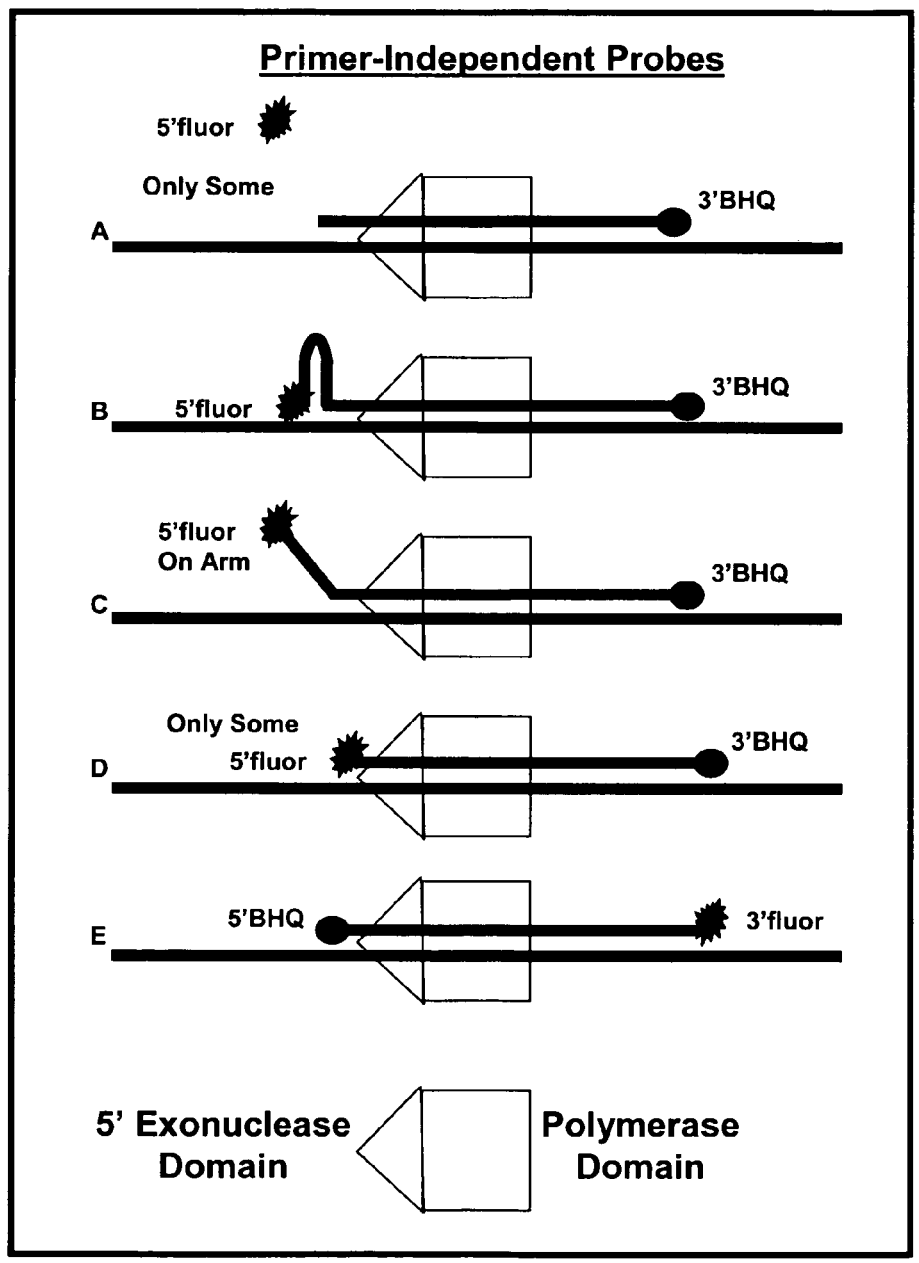
FIG. 1 A schematic illustrating the difference types of probes.

As used herein "sample" can be any material to be tested, such as, for example, a biological or environmental sample. Biological samples can be obtained from any organism. In one embodiment, a sample can be obtained from a mammal, such as a human, companion animal, or livestock. A sample can also be obtained from other animals, such as, for example, a bird. In one embodiment, a sample from an animal comprises a nasopharyngeal aspirate, blood, saliva, feces, urine, or any other bodily fluid. In another embodiment, an environmental sample can be obtained from any environment, such as, for example, soil, water, environments and surfaces in man-made structures.

As used herein "amplification target sequence," "target sequence" and "nucleic acid target sequence" interchangeably mean a DNA sequence that provides a template for copying by an amplification reaction, for example a PCR amplification technique. An amplification target sequence can be single-stranded or double-stranded. If the starting material is RNA, for example messenger RNA, the DNA amplification target sequence is created by reverse transcription of RNA to create complementary DNA (cDNA), and the amplification target sequence is a cDNA molecule. Thus, in a PCR assay for RNA, a hybridization probe hybridizes to and thereby reflects copying of a cDNA amplification target sequence, indirectly signifying the presence of the RNA whose reverse transcription produced the cDNA molecules containing the amplification target sequence. An amplification target sequence is typically bracketed by in length by a pair of primers used in its amplification. An extension product, or "amplicon", whether double-stranded or single-stranded, is defined by the primer pair. An amplification target sequence can be a single nucleic acid sequence. In some cases, however, it may contain allelic variations or mutations and thus not be a single sequence.

As used herein "Tm" refers to the temperature at which half of a subject nucleic acid material exists in double-stranded form and the remainder is single stranded. Historically, the Tm of a primer, probe or amplicon was, a calculated value using either the "% GC" method (Wetmar, J. G. (1991) "DNA Probes: Applications of the Principles of Nucleic Acid Hybridization," Crit. Rev. Biochem. Mol. Biol. 26:227-259) or the "2(A+T) plus 4(G+C)" method, both of which are well known, at a standard condition of primer and salt concentration. LATE-PCR, however, takes into account the actual primer and probe starting concentrations in determining Tm (Sanchez et al. (2004) PNAS (USA) 101: 1933-1938, and Pierce et al. (2005) PNAS (USA) 102: 8609-8614) by using a "nearest neighbor" method (Santa Lucia, J. (1998) PNAS (USA) 95:1460-1465), calculating the Tm using the formula, $Tm=\Delta H/(\Delta S+R \ln(C/2))+12.5 \log [M]-273.15$ (Le Novere, N. (2001), "MELTING, Computing the Melting Temperature of Nucleic Acid Duplex," Bioinformatics 17: 1226-7). $\Delta H$ is the enthalpy and $\Delta S$ is the entropy (both $\Delta H$ and $\Delta A$ calculations are based on Allawi, H. T. and Santa Lucia, J. (1997) Biochem. 36:10581-10594), C is the concentration of the oligonucleotide, R is the universal gas constant, and [M] is the molar concentration of monovalent cations (0.07 in the examples). According to this formula the nucleotide base composition of the oligonucleotide (contained in the terms $\Delta H$ and $\Delta A$), the monovalent salt concentration, and the concentration of the oligonucleotide (contained in the term C) influence the Tm. However, the concentration of magnesium or other divalent cation used in PCR buffers is not included in this formula, and it is known that divalent cation increases Tm. We typically use 3 mM magnesium, which raises probe Tm about 5° Celsius. Therefore, if the desired Tm is 50° Celsius, and 3 mM magnesium is to be used, the above nearest neighbor formula for Tm without magnesium should give a Tm of 45 degrees, which can then be checked empirically, with minor adjustment to the length or composition of the probe as needed. We have found that licensable software, Visual OMP (version 6.1.9) software from DNA Software (Ann Arbor, Mich.) includes such an adjustment to the nearest neighbor formula and yields results close to those that we have determined empirically. References herein to the Tm of a primer or probe means the value that takes into account magnesium concentration unless otherwise stated.

As used herein "allele-discriminating" and "sequence-specific" both refer to the ability of a probe (or in some cases a primer) to selectively hybridize to a perfectly complementary target sequence and to strongly reject closely related sequences having one or a few mismatched bases. As used herein "mismatch tolerant" refers to the ability of a probe (or in some cases a primer) to hybridize to both a perfectly complementary sequence and partially complementary sequences having one or more mismatched bases.

As used herein "single tube" refers to a method comprising a series of at least two operations, for example, sample preparation, amplification or sequencing, that can be performed without transferring the sample from one container, be it a test tube, a reaction well, a chamber in a microfluidics device, a glass slide, or any other apparatus capable of holding a reaction mixture, to another container.

As used herein "exonuclease activity" refers to one of the enzymatic properties of thermostable polymerases, including Taq DNA polymerase, used for PCR amplification. Exonuclease activity refers to a 5' to 3' digestion as distinct from 3' to 5' digestion, which is regarded as a proof reading function of the enzyme. Exonuclease activity is not meant to denote the precise mode or location of cleavage of th DNA sugar phosphate backbone, particularly whether the cleavage is between a moiety attached to the 5' end and the terminal 5' nucleotide, or between the terminal and penultimate 5' nucleotides, or one or more nucleotides downstream of the 3' end. Unless otherwise stated, all polymerases whose use is described herein are understood to include the exonuclease domain, either alone or with the polymerase domain that carries out base pair addition to the 3' end of an upstream primer.

As used herein "primer-dependent" cleavage refers to cleavage of a hybridized oligonucleotide encountered by a polymerase during its extension of a primer. It is known that the presence of a 3' terminal —OH group on the extending strand is required for primer-dependent cleavage. As used herein 'primer-dependent" cleavage also includes cleavage resulting when the 3' OH of an upstream oligonucleotide displaces the 5' end of a downstream oligonucleotide, for example, a hybridized probe, even in the absence of dNTPs. Chemical addition, for example of a phosphate group (capping), and the presence of a terminal 2'3' dideoxynucleotide are known ways to prevent primer-dependent cleavage, as are certain non-natural nucleotides and non-natural inter-nucleotide linkages in the downstream oligonucleotide.

As used herein "primer-independent" cleavage refers 5' to 3' cleavage of a hybridized oligonucleotide by the 5' to 3' exonuclease activity of a polymerase that is not primer-dependent cleavage. In this case the polymerase binds directly to the oligonucleotide/target hybrid and cleaves the 5' end of the bound oligonucleotide. No primer or primer extension is involved.

As used herein, "LATE-PCR" means a non-symmetric DNA amplification employing the polymerase chain reaction (PCR) process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce fluorescently detectable double-stranded amplicon, wherein the concentration-adjusted melting temperature of the Limiting Primer at the start of amplification, $Tm_{[0]}^L$, is not more than 5° C. below the concentration-adjusted melting temperature of the Excess Primer at the start of amplification, $T_{m[0]}^X$, preferably at least as high and more preferably 3-10° C. higher; and wherein thermal cycling is continued for multiple cycles after exhaustion of the Limiting Primer to produce single-stranded product, namely, the extension product of the Excess Primer, sometimes referred to as the "Excess Primer Strand".

As used herein, the term "Low-$T_m$ Probe" means a labeled hybridization probe that signals upon hybridization to its target, which in a LATE-PCR is the Excess Primer-Strand generated by extension of the Excess Primer, and that has a $T_{m[0]}^P$ at least 5° C. below and more preferably at least 10° C. below the $T_{m[0]}$ of the primer that hybridizes to and extends along the Excess Primer-Strand, which in a LATE-PCR is the Limiting Primer. As used herein, a Low-$T_m$ Probe is a linear probe.

B. Detailed Description

Labeled probes and unlabeled oligonucleotides that are modified for particular purposes in DNA amplification reactions, and their use for achieving particular effects during amplification or during post-amplification detection are described. DNA amplification reactions, for example, PCR amplifications, include primer extension by a DNA polymerase. As described herein, probe-target structures comprise a template strand that is longer in the 3' direction than the hybridized probe is in the 5' direction. Thus, probes are recessed from the single-stranded 3' end of the target strand by variable numbers of nucleotides and probes have 5' ends that can either perfectly match the target strand or have extended 5' arms of variable length. Mono-molecular hairpin molecules with these structural features can be used to simulate these constructed as described herein.

In some embodiments, a DNA polymerase must be a thermostable polymerase that does not exhibit target-independent-probe-cleavage or is used in a reaction mixture whose composition that causes it to exhibit target-independent-probe-cleavage. By "exhibit target-independent-probe-cleavage" we mean ability of the enzyme to a cleave an oligonucleotide in the absence of a target sequence, when said oligonucleotide contains a terminal hairpin having a loop 3-5 nucleotides long and a stem 2-5 nucleotides in length, when incubated therewith at 20° C. or less below said enzyme's optimal extension temperature for 10 min. ZO5 Polymerase in a bicine buffer with $Mn^{++}$ is an example of an enzyme that does exhibit target-independent-probe-cleavage. In contrast, Taq DNA polymerase in a reaction mixture containing $Mg^{++}$ and buffered with Sodium Tris is an example of an enzyme that does not exhibit target-independent-probe-cleavage. The method described herein are to be understood to include the use of a polymerase that does not exhibit target-independent-probe-cleavage. Whether or not an enzyme exhibits target-independent-probe-cleavage can be established by using a probe that has a 5' nucleotide extension to the 5' end of the probe wherein said extension forms a hairpin structure having a stem 2-5 nucleotides long by self-annealing at a temperature higher than 70° C. Enzymes that do not exhibit target-independent-probe-cleavage are unable to cleave these hairpin probes in real-time PCR, or end-point isothermal, or end-point oscillating-temperature conditions.

The probes described herein are structurally modified linear, or random coil, DNA hybridization probes that hybridize to a target amplicon strand intermediate the primers and are low-temperature probes that have a $Tm_{[0]}$ that is at least 5° C., preferably at least 10° C., below the mean primer annealing temperature of the amplification reaction in which they are included. If the amplification reaction is, for example, a three-temperature PCR reaction, the probes will not hybridize unless a low-temperature step is added, either at the end, following amplification, or during some amplification cycles, such as during the linear phase of LATE-PCR amplification. Probes that are not cleaved are dual-labeled fluorescent probes having a fluorophore that is quenched when the probe is free in solution, preferably by a non-fluorescent quencher such as DABCYL, a Black Hole quencher or another quencher such as QSY 7 or 9. Black Hole quenchers are proprietary quenchers of Biosearch Technologies, Inc., Novato, Calif. (USA). QSY quenchers are available from Invitrogen Corporation, Carlsbad, Calif. (USA). Probes that are cleaved may also be dual-labeled fluorescent probes, but they need not be. For cleaved probes all that is needed is any way to detect cleaved probe fragments, whether by means of a label on the fragment or some property of the fragment, for example, weight or size or ability to perform a detectable function, such as, for example, causing formation of a color. In this last case, detection of cleavage is indirect.

The blocking oligonucleotides described herein are modified linear oligonucleotides that hybridize downstream (3') to the primers and that are unlabeled.

One type of modified hybridization probe is a probe whose structure is modified to enhance isothermalprimer-independent 5'-exonuclease cleavage when added to a PCR reaction mixture prior to amplification. We refer to such a probe as an "exo-sensitive" or, for short, and EXO-S probe. It is a linear, or random coil, DNA probe that has a Tm at least 5, preferably at least 10° C. below the mean primer annealing temperature in the amplification reaction in which it is used. When subjected to isothermal primer-independent cleavage conditions, it is cleaved at least twice as rapidly, preferably at five times as rapidly and more preferably at least ten times as rapidly as the corresponding unmodified probe.

In one embodiment, the modification that renders the probe exo-sensitive involves covalent linkage of at least one label moiety, for example, a fluorophore or a non-fluorescent quencher to the 5' end of the probe by a chain comprised of at least three contiguous, preferably more than three, and most preferably six contiguous methylene ($CH_2$) groups. Said methylene chain cannot be preceded by, on the end linked to the 5' nucleotide, a carboxyl group, an amine, an amide, or another bulky chemical group, but it is anticipated that said chain of contiguous methylene groups can be preceded by (on the end linked to the 5' nucleotide) an ether group (—O—). In another embodiment, the modification at the 5' end of the probe is comprised of an added nucleotide that is not complementary to the nucleotide of the target that is immediately "upstream" (3') of the hybridized probe. This modification can also be described as a one-base "arm" on the 5' end of the probe. An EXO-S probe may have no 5' arm, that is, no nucleotide that is not complementary to the target or at most a short arm of less than 5 nucleotides, preferably not more than one nucleotide. An EXO-S probe should be designed to form a hybrid that is located more than six nucleotides from the 3' end of its target strand, preferably 10-30 nucleotides from the 3' end. A hybrid more than 40 nucleotides from the end is less preferred, as that slows down target-independent isothermal cleavage of the probe. As a person versed in the art will appreciate, the optimal location for positioning a particular EXO-S probe relative to the 3' end of its specific target will depend on precise conditions and compositions of the amplification reaction in which it is employed; the most important factors being the length of the limiting primer upstream of the EXO-S probe and the base composition of the target sequence to be probed. In all cases, however, the 5' end of the EXO-S probe should not overlap the location on the target strand to which the 3' end of the Limiting Primer hybridized before it was exhausted. In other words, the base on the target strand that is complementary to the 3' end of the limiting primer should be at least two bases upstream of the 5' end of probe, or the 5' end of an arm on the 5' end of the EXO-S probe.

Methods described herein include amplifying at least one DNA target sequence in the presence of an exo-sensitive probe, wherein the amplification process does not include a low-temperature step at which the probe will hybridize, that is, not include incubation at a temperature below the Tm of the probe, until the primer whose extension generates the amplicon strand complementary to the probe is exhausted. When used in a PCR amplification, an EXO-S probe will not hybridize to the amplicon during cycles that have no low-temperature detection step. Non-symmetric PCR methods that include a low-temperature detection step in amplification cycles following exhaustion of the limiting primer, that is, in cycles that generate single-stranded Excess Primer amplicon strands to which the probe is complementary, will result in the probe being hybridized and cleaved in a primer-independent manner, thereby amplifying the signal generated by the probe. If only a post-amplification low-temperature detection step is included, signal from a dual fluorescently labeled probe containing a fluorophore and a quencher, preferably a non-fluorescent quencher, may also continue to rise for 30 min or more, suggesting that repeated hybridization and cleavage occurs during such end-point detection as well as in real-time detection. For this reason end-point readings should be taken after a prescribed time, preferably at least one min and more preferably after at least two min. For example, if the probe is labeled with a fluorophore and a quencher, repeated hybridization and cleavage results in increased production of unquenched fragments and an amplified fluorescence signal. Such methods include homogeneous detection of probe cleavage.

Another type of probe described herein is a probe whose structure is modified to resist primer-independent 5'-nuclease cleavage when added to a PCR reaction prior to amplification. We refer to such probes as "exo-resistant" probes or, for short, EXO-R probes. Exo-resistant probes are low-temperature probes. Exo-resistant probes need not be resistant to primer-dependent exonuclease cleavage. Certain embodiments, however, are resistant to both primer-independent 5' exonuclease cleavage and primer-dependent 5' exonuclease cleavage. Exo-resistant probes resist primer-independent cleavage to the extent that, if labeled with a fluorophore and a quencher, hybridized to complementary target strands, and subjected to isothermal primer-independent 5' nuclease cleavage conditions, there is not an appreciable rise in fluorescence, not more than 10%, over a 25 minute period. Some embodiments remain resistant even when subjected to rapid thermal oscillation about the probe-target Tm, as described below, while other embodiments can be cleaved by such oscillation to generate an amplified signal. Exo-resistant probes are linear, or random coil, hybridization probes whose unmodified structure is a labeled or unlabeled DNA oligonucleotide. One modification to render a probe exo-resistant is to link a label moiety, for instance a fluorophore or a non-fluorescent quencher, to the 5' terminal nucleotide by other than a methylene chain. Another modification to render a probe exo-resistant is to add a 5' terminal arm comprising from two to seven nucleotides that do not hybridize to the probe's target. Yet another modification to render a probe exo-resistant is to add a nucleotide extension to the 5' end of the probe wherein said extension forms a hairpin structure having a stem 2-5 nucleotides long by self-annealing at a temperature higher than 70° C. These 5' hairpins also resist oscillating-temperature-induced cleavage.

Methods described herein include amplifying at least one DNA target sequence by a non-symmetric PCR amplification method, preferably a LATE-PCR method in the presence of an exo-resistant probe, wherein the amplification process does not include a low-temperature step at which the probe will hybridize until after exhaustion of the Limiting Primer. When used in a PCR amplification, an EXO-R probe will not hybridize to the amplicon during cycles that have no low-temperature detection step. PCR methods that include a low-temperature detection step following amplification or, for non-symmetric methods, following exhaustion of the limiting primer will result in the probe being hybridized. If detection is isothermal, that is, without rapid temperature oscillation about the probe's Tm, the probe will not be cleaved, and its signal will be that resulting from hybridization only. In such embodiments the probe must emit a detectable upon hybridization. If detection is end-point and includes rapid thermal oscillation about the probe's Tm, for example from 5° C. above the Tm to 5° C. below, or preferably from 10° C. above to 10° C. below, wherein each oscillation-cycle takes 30 sec or less, certain embodiments will be cleaved in a primer-independent manner, as stated above, but other embodiments will not cleaved. Cleavage by rapid oscillation in a primer-independent manner will increase the rate at which the probe signal is generated. In these embodiments cleavage generates a signal directly or indirectly, as described above for exo-sensitive probes. The magnitude of the signal at any given point in time will depend on the rate of cleavage and the total amount of the probe in the reaction. For example, if the probe is labeled with a fluorophore and a quencher, repeated oscillation results in increased production of unquenched fluorophore-containing fragments and an amplified fluorescence signal until all available probe is cleaved. Such methods include homogeneous detection of probe hybridization or probe cleavage.

Also described herein are structurally modified oligonucleotides that hybridize to a complementary strand and form a hybrid that is resistant both to primer-dependent 5' nuclease cleavage and primer-independent 5' nuclease cleavage. We sometimes refer to such oligonucleotides as EXO-N oligonucleotides. An EXO-N is a linear oligonucleotide that has a Tm sufficiently high to hybridize to a target strand downstream from one of the primers during the primer-extension step of a PCR amplification reaction in which it is used, either a symmetric PCR amplification or a non-symmetric PCR amplification. Because it is not cleaved by the polymerase during primer extension, it inhibits extension of the strand to which it is hybridized, thereby rendering amplification of that strand inefficient. One modification of a linear oligonucleotide that renders it an EXO-N oligonucleotide is to add an oligonucleotide extension to the 5' end of a linear oligonucleotide that is not complementary to the oligonucleotide's target and that such extension forms a hairpin structure that has a stem 2-5 nucleotides in length and has a Tm of at least 70° C.

Methods described herein include performing a symmetric or non-symmetric PCR amplification reaction in the presence of an EXO-N oligonucleotide that is specific for one possible target allele that would otherwise be amplified by the primer pair used, thereby favoring amplification of one or more alternative allelic variant sequences to which the EXO-N oligonucleotide does not hybridize during primer extension. Methods described herein also include inserting an EXO-N oligonucleotide into a symmetric PCR amplification reaction at a desired point, that is, after two or more thermal cycles, to render amplification of one strand inefficient, either the plus strand or the minus strand, and thereby to favor in subsequent cycles amplification of the other strand.

DNA amplification by polymerase chain reaction (PCR) methods for DNA amplification target sequences (including cDNA sequences), specifically non-symmetric PCR methods such as asymmetric PCR and LATE-PCR in which one primer, the Excess Primer, is present is substantial excess compared to the other primer, the Limiting Primer, at least 5:1 and preferably at least 10:1 are described. Our preferred amplification method is LATE-PCR, but other methods can be used.

In some embodiments, the methods utilize modified low-temperature DNA hybridization probes. DNA hybridization probes are non-extendable DNA oligonucleotides that are complementary to their target, which in this case is a DNA sequence in the extension product of the Excess Primer (the Excess Primer strand), of the amplicon produced by the PCR amplification reaction. The unmodified probes are or contain a stretch of DNA, the target complementary sequence of the probe. The probe's target complementary sequence may be perfectly complementary to an Excess Primer strand that may be produced in the reaction, imperfectly complementary to at least one Excess Primer strand that may be produced in the reaction, or both. The probe will have a higher Tm (in the case of LATE-PCR, $Tm_{[0]}$) against a perfectly complementary target than against an imperfectly complementary target. For example, if the probe is designed to have a Tm against a perfectly complementary target of 55° C., its Tm against a target containing one or more mismatched bases, a nucleotide deletion or a nucleotide insertion will be lower, sometimes by 10° C. or more. This allows a probe to distinguish among targets by the Tm of the hybrid or hybrids formed. In all embodiments of this invention the probes are low-temperature probes.

Non-symmetric PCR methods that utilize probes include the probes in the starting amplification reaction mixture, which also includes primers, dNTPs, buffer, a thermostable DNA polymerase, and, if the nucleic acid starting material is RNA, reverse transcriptase. Any probe that is not to be cleaved during or at the end of amplification will be a dual fluorescently labeled probe that emits a detectable fluorescent signal upon hybridization. Suitable labeling schemes are known in the art. Our preferred labeling is a fluorophore covalently linked to one terminus and a non-fluorescent quencher covalently linked to the other terminus, but other labeling methods can be used. Numerous quenchers are known in the art, including DABCYL, DABMI, Black Hole quenchers, QSY quenchers, Deep Dark quenchers available, and others. Any probe that is to be cleaved as part of detection may be similarly labeled, but it need not be. All that is required for such a probe is that cleavage be detectable, so the probe can be singly labeled with a detectable label, or it can be unlabeled.

Probes used can be linear, or random coil, DNA hybridization probes that are modified either to enhance or substantially eliminate their primer-independent, isothermal 5' nuclease cleavage when hybridized to target during PCR amplification, that is, for real-time detection, or following amplification, that is, for end-point detection. As indicated, we refer to probes with enhanced cleavability as exo-sensitive or EXO-S probes, and we refer to probes that are resistant to cleavage as exo-resistant or EXO-R probes. EXO-R probes remain substantially uncleaved when subjected to isothermal primer-independent cleavage conditions for 25 minutes. Some EXO-R probes can be cleaved by rapid temperature oscillation about the Tm of the probe-target hybrid, while others resist even such oscillation. Detection occurs after exhaustion of the Limiting Primer, so any cleavage that occurs is due to primer-independent 5' nuclease enzyme activity. EXO-S and EXO-R probes are low-temperature probes.

Modifications to a random-coil DNA probe to make it an EXO-S probe are to add a 5' nucleotide that is not complementary to the probe's target and to link to the probe's 5' nucleotide a label moiety, preferably a fluorescent moiety, by a methylene chain of at least three and preferably six methylene groups.

Modifications to a random-coil DNA probe to make it an EXO-R probe can be considered to be three classes based on structural modifications of their 5' ends:

Class (1) Addition of certain non-nucleic acid chemical moieties to the 5' end of an oligonucleotide probe whose 5' end is hybridized to a fully complementary target sequence;

Class (2) Addition of one or more noncomplementary nucleotides to the 5' end of an oligonucleotide probe, such that the 5' end of the probe is not complementary to the target sequence and therefore forms a single-stranded "arm" that is extended for one or more bases;

Class (3) Addition of a plurality of noncomplementary nucleotides to the 5' end of the oligonucleotide probe, such that the single-stranded "arm" at the 5'-end forms a hairpin structure having a stem of 3-5 nucleotides and an self-annealing $T_m$ of >70° C.

Figure 2:
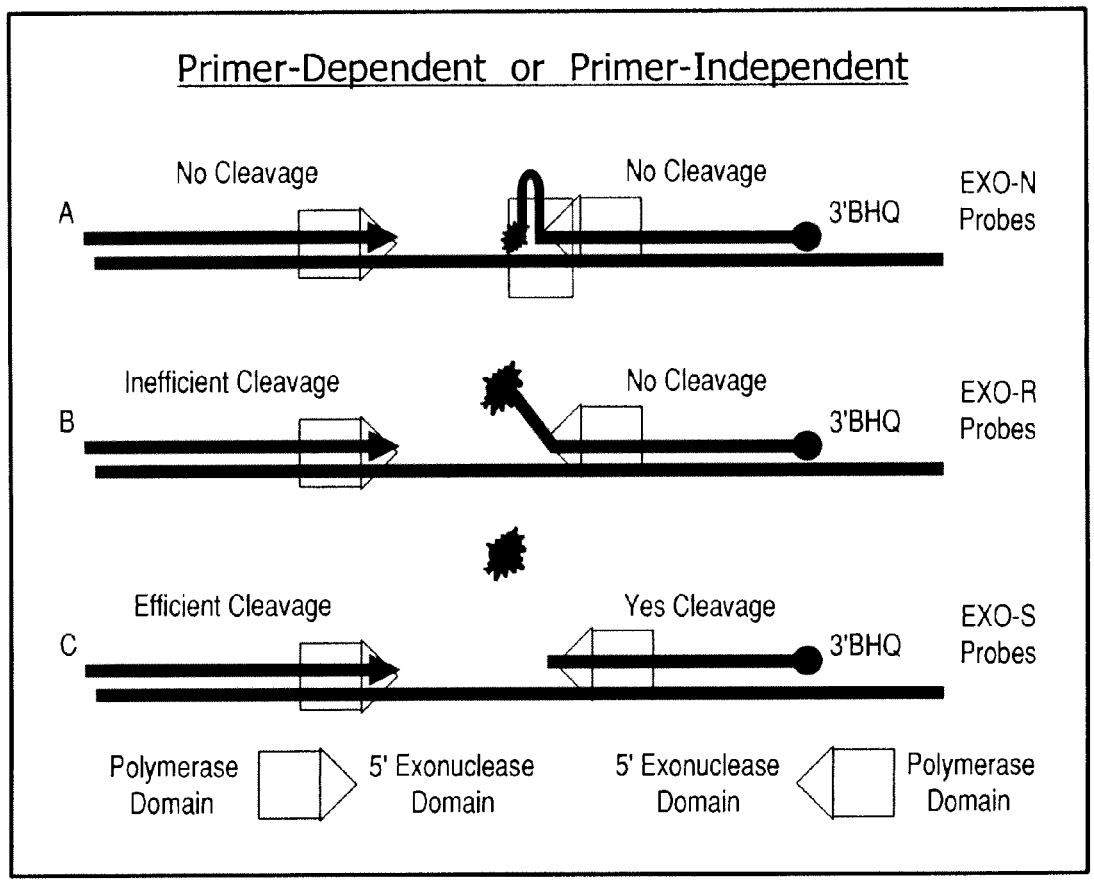
FIG. 2 A schematic illustrating various mechanisms of cleavage for the probes shown in FIG. 1.
Figure 3:
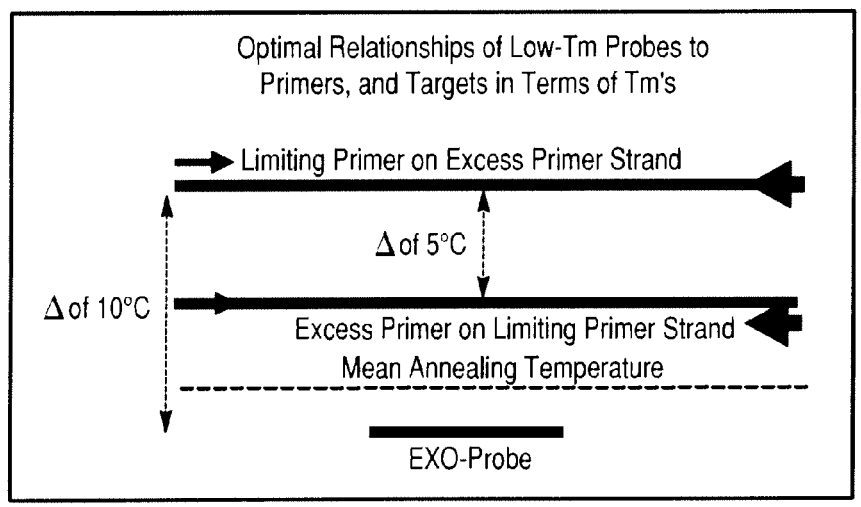
FIG. 3 A schematic illustrating optimal Tm relationships for a low-temperature probe relative to primers and targets.

FIG. 1 shows examples of each class of EXO-R probes along with an exemplary 5' nuclease probe for comparison. FIG. 2 shows an exemplary cleavage mechanism for the Class (1)-(3) probes.

In a Taq system, for example, some Class (1) and Class (2) EXO-R probes could be cleaved by primer-dependent cleavage were the $T_m$ of the probe-target hybrid was not sufficiently low to avoid probe binding in the path of extending primer. In contrast, the Class (3) probes would not be cleaved by an extending primer if the Tm of the probe-target hybrid was not sufficiently low to avoid probe binding in the path of the extending primer and would render primer extension inefficient.

To determine whether a particular modified random-coil probe is an EXO-S or EXO-R probe, its cleavability can be compared to that of the corresponding unmodified probe when subjected to PCR amplification reaction conditions followed by isothermal primer-independent cleavage conditions. To determine whether an EXO-R probe is or is not cleavable by rapid temperature oscillation around its Tm, its cleavage can be plotted as a function of time or number of temperature cycles.

EXO-S and EXO-R probe methods are, as has been stated, non-symmetric PCR amplifications plus detection of hybridized probes or detection of cleaved probe fragments. If the probes emit a detectable signal, for example, a fluorescent signal, due to being hybridized or due to being cleaved, detection can be performed during the amplification reaction (real time) or after completion of the reaction (end point) by means of a low-temperature detection step that may or may not include oscillation. Detection with such probes may also include generation of a melt curve for probe-target hybrids.

The following descriptions illustrate how several EXO-S probes, or several EXO-R probes having the same or different labels can be added to multiplexed PCR reactions to increase the amount of information that such reactions generate. A similar outcome can be achieved by combining EXO-S probes and EXO-R probes in the same reaction.

Multiplexed non-symmetric PCR reactions can be built to use several pairs of primers, each for a different target sequence. Each of the resulting single-stranded amplicons can be detected by dropping the temperature during the reaction or at the end of the reaction to achieve hybridization of one or more EXO-S probes to its complementary sequence in the single-stranded target amplicon. If each of the EXO-S probes is labeled with a different colored fluorophore, or with a different moiety having a unique molecular weight or electrical signature, each of the probe-amplicon hybrids will generate its own unique signal. However, two EXO-S probes can also be labeled with the same signaling group, provided they form probe-amplicon hybrids at different temperatures. Similarly an EXO-S probe can be used with an EXO-R probe of the same color but a distinguishably different Tm, in which case the distinction can be increased if the EXO-R probe is cleavable by temperature oscillation, as only one of the probes is cleaved during isothermal incubation of the probes and amplicons, the second probe being cleaved during subsequent or prior oscillation of the temperature.

The repertoire of possible targets that generate distinct signals with EXO-S probes can be increased still further by utilizing the principle of "Color Triplet Coding" described by Kramer (U.S. Pat. No. 6,150,097). In this case each amplicon, either a unique sequence or an allelic variant, is targeted with its own EXO-S probe that is labeled with either two or three different 5' labels. Thus, when a probe-amplicon hybrid is formed and cleaved two or three labels are released via cleavage. As described by Kramer there are multiple ways to combine multiples labels in groups of two or three.

Similarly, multiplexed asymmetric PCR reactions can be built using several pairs of primers to generate multiple single-stranded amplicons that are detected with multiple EXO-R probes when the temperature is dropped during or at the end of the reaction. In this case each of the EXO-R probes can be labeled with a differently colored fluorophore. In addition, each EXO-R probe can either be sequence specific, i.e. allele discriminating, or mismatch tolerant, depending on its length. In this case the best way to distinguish probe-amplicon hybridization is to carryout a melting curve analysis in which the temperature of the reaction is either lowered gradually, or increased gradually from a preset low temperature. Under these circumstances each EXO-R probe displays its own unique melting profile and the combination of two EXO-R probes of the same color results in a composite melting curve. In addition, an EXO-R probe that is resistant to temperature oscillation and an EXO-R probe that is sensitive to temperature oscillation can be multiplexed, as temperature oscillation will alter the signal of only one of the probes.

The repertoire of possible targets that generate distinct signals with EXO-R probes can be increased still further by utilizing the principle of "Color Triplet Coding" described by Kramer (U.S. Pat. No. 6,150,097). In this case each amplicon, either a unique sequence or an allelic variant, is targeted with its own EXO-R probe that is labeled with either two or three different 5' labels. Thus, when a probe-amplicon hybrid is formed and melted, it generates the same melting curve in two or three colors. As described by Kramer there are multiple ways to combine multiples labels in groups of two or three.

Yet another means of using EXO-S and EXO-R probes involves combining them in a single multiplexed asymmetric PCR reaction. In this case different probes can detect different single-stranded amplicons by either melt curve analysis or cleavage analysis. For instance, a mismatch tolerant EXO-R probe can be labeled with a colored fluorophore that generates a unique melt curve as the temperature of the reaction is dropped. Once maximum binding of the EXO-R probe to its target is reached at a low temperature the reaction temperature can be dropped still further to achieve hybridization and isothermal or oscillating-temperature dependent cleavage of an EXO-S probe, which may be in the same color, to its target and would have a lower Tm than that of the EXO-R probe to its target. Detection of the EXO-S probe cleavage products can be carried out at the low temperature but, preferably is carried out at an upper temperature, for instance 70° C. at which neither the EXO-S probe nor the EXO-R probe is hybridized to its target. Because of the presence of the quencher on each of these linear probes, only the fluorophore cleaved from the 5' end of the EXO-S probe generates a signal above background at the upper temperature.

EXAMPLES

Figure 4:
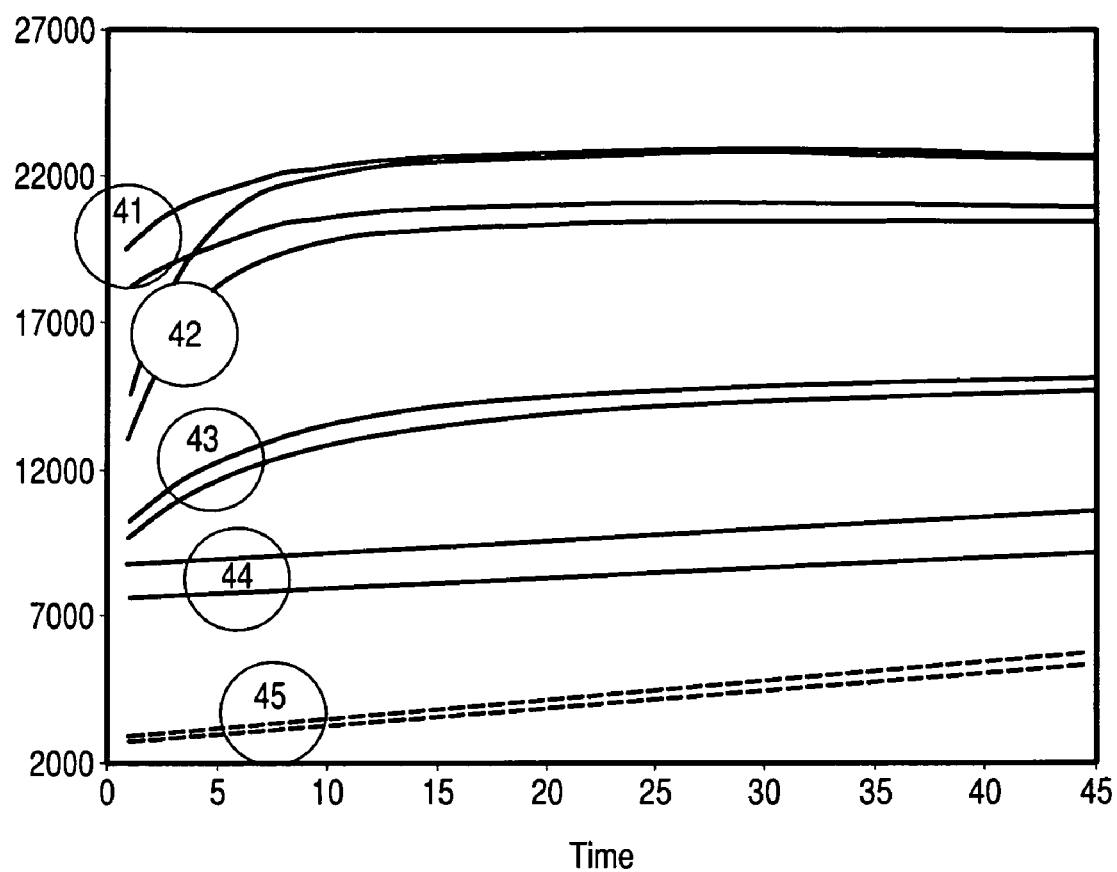
FIG. 4 The capacity of Z05 to cleave various probe structures.

Example 1 (FIG. 4)

This example demonstrates that under the conditions used here polymerase ZO5 fails to exhibits primer-independent resistance.

The amplification reactions each contain, 1×RT-PCR buffer (Roche Diagnostic), 50 mM bicine/KOH, pH 8.2 (25° C.), 115 mM K-acetate, 8% glyercol (v/v), and 3 mM Manganese Acetate (Mn OAc$_2$). ZO5 polymerase concentration is 200 units per reaction, the probes at 0.5 µM and the complementary target at 1.5 µM. The reaction is isothermal and run at 52° C. Fluorescence data is collected for 15 minutes at 20 second intervals. Reactions are run using an ABI 7700 thermocycler.

The following probes and their complementary targets were used:

| Probe Name | Sequence (5'-3') |
| --- | --- |
| Linear FT (no arms) | Fam-CCATGATACAAGCTTCC-BHQ1 (SEQ ID NO: 1) |
| Linear FT BHQ 5' | BHQ1-CCATGATACAAGCTTCC-Fam (SEQ ID NO: 1) |

-continued

| | Sequence (5'-3') |
|---|---|
| Linear FT (5'3'arms) | Fam-TTTTTTCCATGATACAAGCTTCCTT TTTT-BHQ1 (SEQ ID NO: 2) |
| 0-4-0 MW-BG | Fam-CGGTGAAAACCGCGCCTGCAATATA CAGC-BHQ1 (SEQ ID NO: 3) |
| Target Names | |
| FT target | ACTTAGTAATTGGGAAGCTTGTATCATGG CACTTAGAACCT (SEQ ID NO: 4) |
| BG target | AAAAAAGCTGTATATTGCAGGCGAAAAAA (SEQ ID NO: 5) |

The following probe-target combinations were tested (each in duplicate). The two (41) lines with the fastest rate of cutting is the FT target+Linear-FT Probe with 5'3' arms of 6 non-complementary nucleotides (all Ts). The two (42) lines with the second highest rate of cutting is the FT target+Linear-FT Probe without 5'3' arms. The two (43) lines are the BG target+0-4-0 MW-BG probe which contains a 5' hairpin with 4-bp stem and 3 base loop. All three of the above probes have a 5' FAM fluorophore.

The two (44) lines are the FT target+Linear-FT Probe without 5'3' arms, but the Black Hole Quencher 1 is on the 5' end.

The two (45) dotted lines are the 0-4-0 MW-BG Probe with the 5' hairpin but no BG target was added to the reaction.

The results shown in FIG. 4 demonstrate that under these conditions Polymerase ZO5 cleaves the 0-4-0 MW-BG Probe with the 5' hairpin, even in the absence of the BG target. All of the other probes were not cleaved in the absence of their target sequences (results not shown). Thus, these results demonstrate that Polymerase ZO5 under these conditions exhibits target-independent-probe-cleavage. This conclusion is supported by the fact that under these conditions Polymerase ZO5 also cleaved the Linear-FT Probe with 5'3' arms of 6 non-complementary nucleotides (all Ts) when it is bound to its FT target even though this EXO-R probe is not cleaved by Taq Polymerase.

Figure 5:
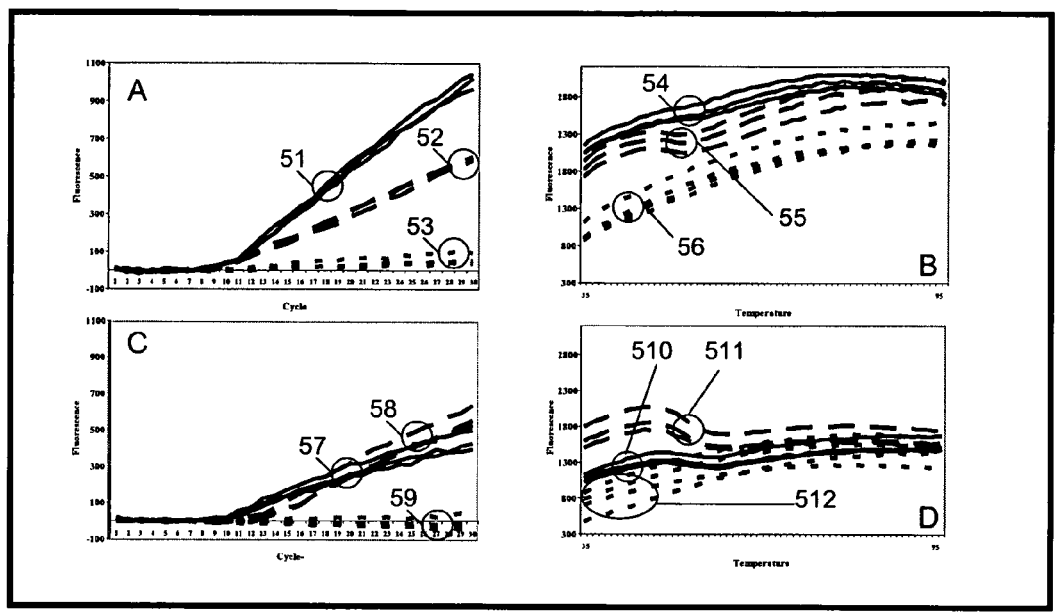
FIG. 5A: ZO5 Polymerase, amplification of 10,000 Copies of H5 detected with TET EXO-R probe and H3 detected with FAM EXO-R probe.
FIG. 5B: Melt curves for FIG. 5A.
FIG. 5C: Platinum Taq Polymerase, amplification of 10,000 Copies of H5 detected with TET EXO-R probe and H3 detected with FAM EXO-R probe.
FIG. 5D: Melt curves for FIG. 5B.

Example 2 (FIG. 5(A-D))

In this example, we show that the enzyme ZO5 polymerase, which exhibits target-independent-probe-cleavage (Example 1), cleaves EXO-R probes while Platinum Taq polymerase, which does not exhibit target-independent-probe-cleavage, does not cleave EXO-R probes. FIG. 5 shows the results of four experiments for the detection of the H5 and H3 influenza genes starting with 10,000 copies of each run under the same reaction conditions where the only change is the enzyme used in the polymerization reaction. The H5 gene is detected by a 5'TET EXO-R probe (solid line) and the H3 gene by a 5' FAM EXO-R probe (hashed line). NTC values are shown as dotted lines.

FIG. 5A shows the results with the ZO5 enzyme for the LATE-PCR amplification where (51) is the TET probe fluorescence, (52) the FAM probe fluorescence, and (53) the NTC results with both TET and FAM probes.

FIG. 5B shows the melt of the probes, where (54) is the TET probe fluorescence, (55) the FAM probe fluorescence, and (56) the NTC results for both the FAM and TET probes.

FIG. 5C shows the LATE-PCR amplification results using Platinum Taq polymerase as the enzyme, where (57) is the TET probe fluorescence, (58) the FAM probe fluorescence, and (59) the NTC TET and FAM probe fluorescence.

FIG. 5D shows the melt of the probes, where (510) is the TET probe fluorescence, (511) the FAM probe fluorescence, and (512) the NTC TET and FAM probe fluorescence.

The LATE-PCR seems more efficient in the ZO5 example (FIG. 5A) where the Ct values are 29 for both genes, while for Platinum Taq (FIG. 5C) the Ct values are 30(H5) and 33(H3). However, this is not the case as shown by the two melt curves. The TET probe (54) in the ZO5 reaction is getting completely cut releasing free TET into the reaction, while the FAM probe (55) with ZO5 is partially cut. This can be seen in FIG. 5B where in the ZO5 reaction probe melt curves, the probe fluorescence (54, 55) does reach the NTC fluorescence value (56) when the probe is no longer bound to target. This also results in lower Ct values in the amplification. The result is quite different in the Platinum Taq reactions (FIG. 5D) where the probe melt curves show no free TET (510) or FAM (511) when the probe is no longer bound to target. The Ct values (FIG. 5C) therefore are later since no free FAM or TET is detected.

EXO-R Probes:

| EXO-R Probes: | |
|---|---|
| 5' TET-CACTAGGGAACTCGCTG-BHQ1 3' (SEQ ID NO: 6), | Tm = 52.7(H5) |
| 5' FAM-CGTTTCTCGAGGTCCTGCG-BHQ1 3' (SEQ ID NO: 7), | Tm = 54.5(H3) |
| Limiting Primers: | |
| 5' AAGGATAGACCAGCTACCATGATTGCC 3' (SEQ ID NO: 8), | Tm = 66.8(H5) |
| 5' CGTTGTATGACCAGAGATCTATTTTAGTGTCC T 3' (SEQ ID NO: 9), | Tm = 67.9(H3) |
| Excess Primers: | |
| 5' ATAAGTGGAGTAAAATTGGAATCAATAGG 3' (SEQ ID NO: 10), | Tm = 63.6(H5) |
| 5' CCATCAGATTGAAAAAGAATTCT 3' (SEQ ID NO: 11), | Tm = 62.7(H3) |

Reaction Conditions (concentrations in millimolar (mM) or micromolar (μM), volumes in microliters (μL):

| | |
|---|---|
| 10x PCR Buffer 1x | 2.5 μL |
| 10 mM dNTPs 250 μM | 0.625 μL |
| 50 mM Mg$^{++}$ 3 mM | 1.5 μL |
| 10 μM Limiting Primer 2x | 0.125 μL |
| 100 μM Excess Primer 2x | 0.250 μL |
| 10 μM Probes 500 nM 2x | 1.25 μL |
| 10 μM C3 Primesafe 500 nM | 1.50 μL |
| Total Mix: | 9.375 μL |
| ZO-5 (5units), Platinum TAQ (1.25 u): | 1.0/0.25 final units |
| Water: | 12.625 μL or 13.375 μL |
| DNA Amplicons (2 at 10,000 copies/μL) | 2.0 |
| Total Volume: | 25.0 μL |

Thermal Conditions: (annealing ZO-5=58° C., Taq=62° C.)
Stage 1: 95° C./3:00 minutes
Stage 2: (95° C./10 secs: 58° C. or 62° C. for 15 secs: 72° C. for 30 secs) Repeat 20 times Stage 3: (95° C./10 secs—58° or 62° C./15 secs—72° C./30 secs—45° C./20 secs) Repeat 30 times
Stage 4: Melt 35° C.-94° C.

Example 3 (FIG. 7A-I)

EXO-N Probes in Primer-Dependent and Primer-Independent LATE-PCR Reactions

In this example we show that a 5' Hairpin EXO-R Probe is not cleaved by TAQ polymerase in a primer-dependent manner during the initial cycles of LATE-PCR cycles and is not cleaved in a primer independent manner when the limiting primer is exhausted. Furthermore, depending on the Tms of the pair of LATE-PCR primers used, the EXO-R probe renders amplification of the BG target inefficient. Results are shown in FIG. 7A-I.

Figure 7:
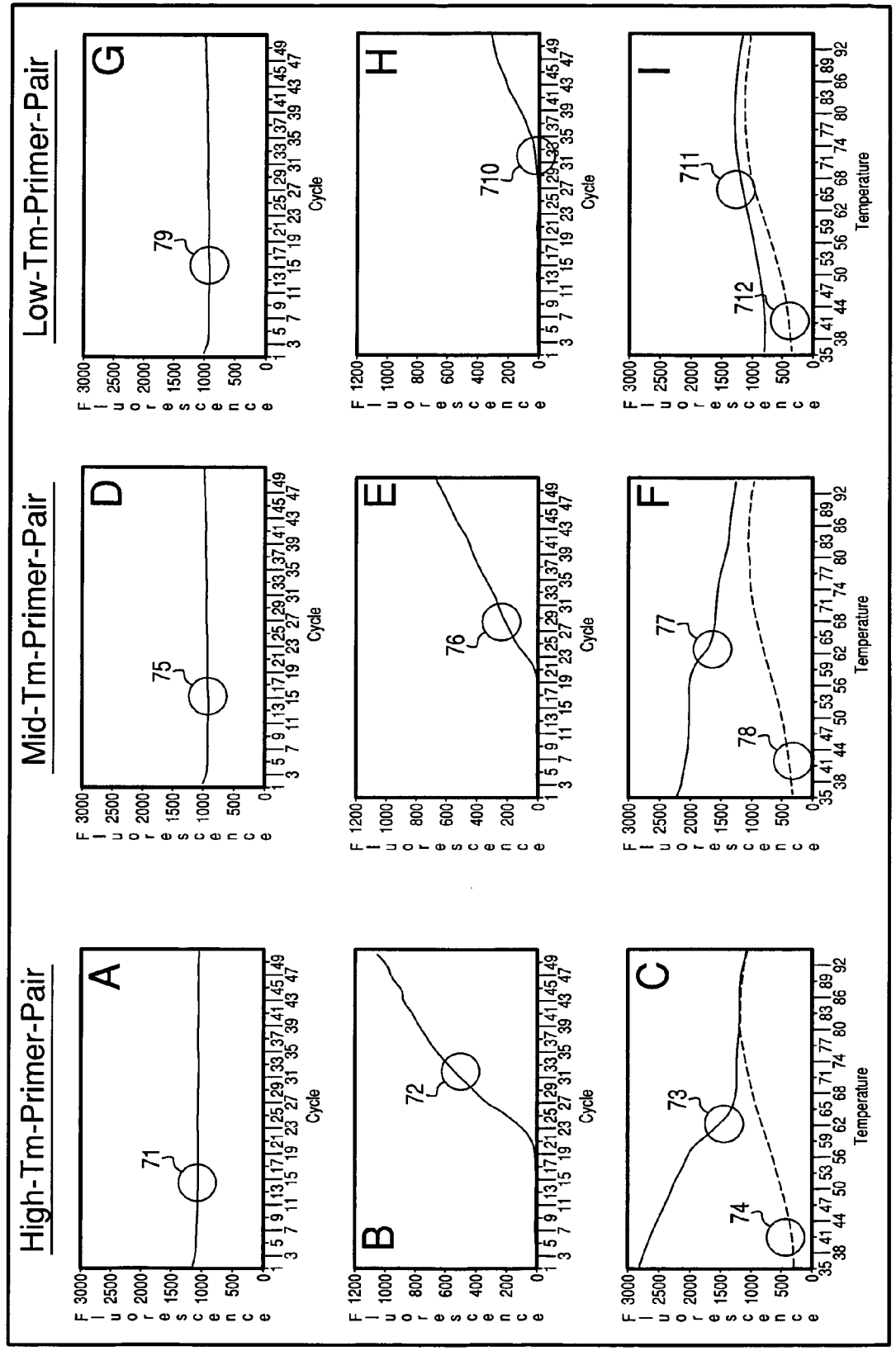
FIG. 7A: 95° C. analysis of BG Probe downstream of EXO-R oligonucleotide in real-time LATE-PCR assay with High-Tm-Primer Pair.
FIG. 7B: 45° C. analysis of BG Probe downstream of EXO-R oligonucleotide in real-time LATE-PCR assay with High-Tm-Primer Pair
FIG. 7C: End-point melt curve analysis of BG Probe downstream of EXO-R oligonucleotide LATE-PCR assay with High-Tm-Primer Pair.
FIG. 7D: 95° C. analysis of BG Probe downstream of EXO-R oligonucleotide in real-time LATE-PCR assay with Mid-Tm-Primer Pair.
FIG. 7E: 45° C. analysis of BG Probe downstream of EXO-R oligonucleotide in real-time LATE-PCR assay with Mid-Tm-Primer Pair.
FIG. 7F: End-Point Melt curve analysis of BG Probe downstream of EXO-R oligonucleotide LATE-PCR assay with Mid-Tm-Primer Pair.
FIG. 7G: 95° C. analysis of BG Probe downstream of EXO-R oligonucleotide in real-time LATE-PCR assay with Low-Tm-Primer Pair.
FIG. 7H: 45° C. analysis of BG Probe downstream of EXO-R oligonucleotide in real-time LATE-PCR assay with Low-Tm-Primer Pair.
FIG. 7I: End-Point Melt curve analysis of BG Probe downstream of EXO-R oligonucleotide LATE-PCR assay with Low-Tm-Primer Pair.

FIGS. 7A-C shows results for the High-Tm-Primer Pair: FIG. 7A real-time analysis at 95° C., FIG. 7B real-time analysis at 45° C., FIG. 7C end-point melt curve analysis ((73) Probe with target, (74) Probe alone). FIGS. 7D-F shows results for the Mid-Tm-Primer Pair: FIG. 7D real-time analysis at 95° C., FIG. 7E real-time analysis at 45° C., FIG. 7F end-point melt curve analysis ((77) Probe with Target, (78) Probe Alone)). FIGS. 7G-I shows results for the Low-Tm-Primer Pair: FIG. 7G real-time analysis at 95° C., FIG. 7H real-time analysis at 45° C., FIG. 7I end-point melt curve analysis ((711) Probe with Target, (712) Probe alone).

FIGS. 7A, 7D, 7G show that the signal of the probe does not change at 95° C. over 50 cycles with any primer pair. This result indicates that the EXO-R probe was not cut by a primer-dependent mechanism and further shows that during LATE-PCR that the EXO-R probe was not cut by primer-independent cleavage. FIGS. 7B, 7E, 7H shows real-time results of the probe fluorescence at 45° C. after the extension step at 72° C. for the three primer pairs. In the case of the High-Tm-Primer Pair (FIG. 7B) the EXO-R probe is not bound and does not block the amplification. In the case of the Mid-Tm-Primer Pair (FIG. 7E) the EXO-R probe begins to block amplification as seen by a delay in Ct and a decrease in signal intensity. In the case of the Low-Tm-Primer Pair (FIG. 7H) the EXO-R probe significantly inhibits amplification as seen by major delay in $C_t$ and a major decrease in signal intensity. FIGS. 7C, 7F, 7I show the melt curves of the EXO-R FAM probe 35C-94C for each of the primer examples. In 7C the largest amount of PCR product is shown, while 7F a smaller amount is shown due to the blocking ability of the EXO-R probe, and in (7I) almost no PCR products are produced. Since melt curves are done after the LATE-PCR, no free FAM is detected indicating that the probes were not cut in a primer dependent or independent manner. The solid black lines indicate the reaction with 10,000 copies of BG starting copies, while the dotted black lines indicate the NTCs.
Sequences:

Limiting Primers:

```
TGCGTTCTGACTGAACAGTGATCGAG    Tm = 72° C.
(SEQ ID NO: 12),              (High-Tm-Primer Pair)

TTCTGACTGAACAGCTGATCGAG       Tm = 64° C.
(SEQ ID NO: 13),              (Mid-Tm-Primer Pair)

TGACTGAACAGCTGATCGAG          Tm = 61° C.
(SEQ ID NO: 14),              (Low-Tm-Primer Pair)
```

-continued

Excess Primers:

```
CCCTCTTGAAATTCCCGAATGG        Tm = 66° C.
(SEQ ID NO: 15),              (High-Tm-Primer Pair)

TCTTGAAATTCCCGAATGG           Tm = 61° C.
(SEQ ID NO: 16),              (Mid-Tm-Primer Pair)

TTGAAATTCCCGAATGG             Tm = 58° C.
(SEQ ID NO: 17),              (Low-Tm-Primer Pair)
```

EXO-R Probe 04017:

```
5' FAM-CGCTGAAAGCGCGCCTGCAA   Tm = 60 C.
TTTACAGC-BHQ1 3'
(SEQ ID NO: 18),
```

Reaction Conditions: microliters (μL)

| | | | | |
|---|---|---|---|---|
| 10x | PCR Buffer | 1x | | 2.5 μL |
| 10 mM | dNTPs | 250 uM | | 0.625 μL |
| 50 mM | Mg++ | 3 mM | | 1.5 μL |
| 10 uM | Limiting Primer | 50 nM | | 0.125 μL |
| 100 uM | Excess Primer | 1000 nM | | 0.250 μL |
| 10 uM | EXO-N Probe | 100 nM | | 0.250 μL |
| 10 uM | Primesafe9-3DD | 500 nM | | 1.250 μL |
| 1.25 U | Platinum TAQ | | | 0.250 μL |
| | Water | | | 17.25 μL |
| | BG Target | $10^4$ Copies/μL | | 1.0 μL |
| | Total | | | 25 μL |

Thermal Conditions:
Stage 1: 95° C. for 5 min.
Stage 2: Repeat 50 Cycles, 95° C. for 10 sec, 61°/58° C. for 15 sec, 72° C. for 20 sec, and 45° C. for 20 sec.
Stage 3: Melt 35° C.-94° C.

Figure 8:
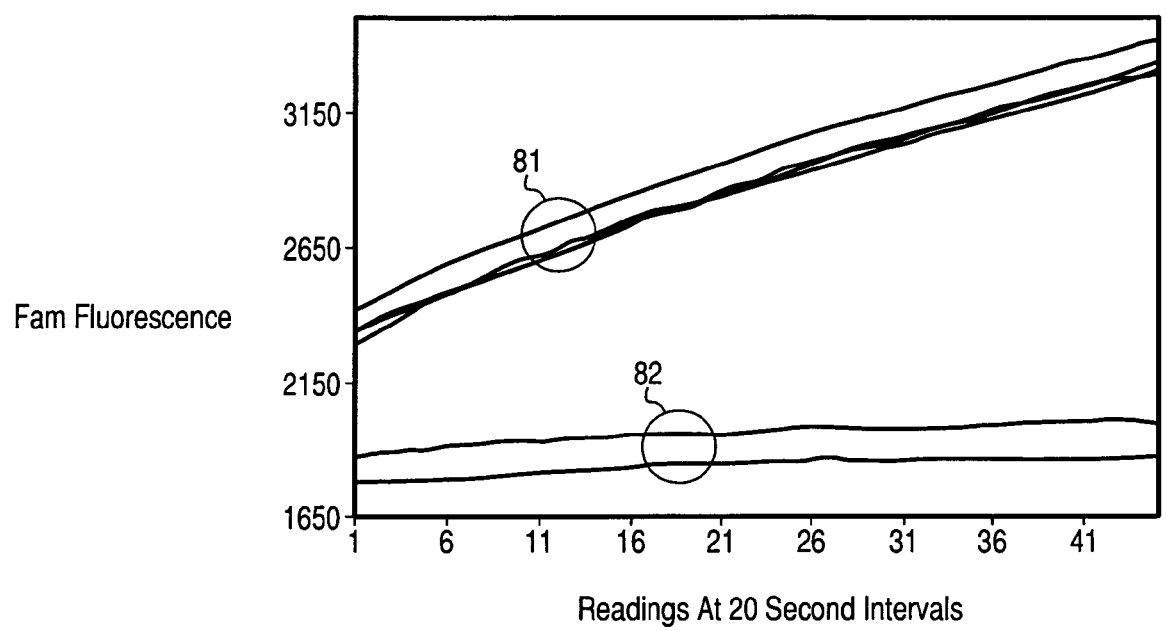
FIG. 8: EXO-S Probe using a FAM on the 5' terminus.

Example 4 (FIG. 8)

EXO-S Probe Using a FAM on the 5' Terminus

FIG. 8 for example 4 shows EXO-S probe signal amplification by oscillation for 15 minutes after the completion of a LATE-PCR reaction. The reactions conditions were 45 rounds of 10 seconds at 95° C., 10 seconds at 64° C. and 20 seconds at 72° C. The final reagent concentrations were 1× Invitrogen PCR buffer, 3 mM Mg++, and 1.25 units of Invitrogen Taq polymerase, 200 nM of dNTPs, 50 nanomolar (nM) FT#2 limiting primer, 1000 nM FT#2 excess primer and 0.6× of PrimeSafe™ #022 (PrimeSafe is a reagent available from Smiths Detection, Inc. and 300 nM FT MBseq4 in a volume of 25 mircoliters (μL).

The sequence of the FT#2 limiting primer was (SEQ ID NO: 19)
5' GGAAGTGTAAGATTACAATGGCAGGCTCCAGA 3'.

The sequence of the FT#2 excess primer was

5' GTTGCCCAAGTTTTATCGTTCTTCTCA 3'. (SEQ ID NO: 20)

The FT MBseq4 EXO-S Probe was

5'FAM-CATGATACAAGCTTC-BHQ1 3'     (SEQ ID NO: 21)

After the completion of PCR; 45 rounds of oscillating between 45° C. (10 secs) and 65° C. (20 secs). The fluorescence was collected at 65C. The lines (81) are replicates that contain both FT MBseq4 probe and amplified FT product while lines (82) are no template control samples.

Figure 9:
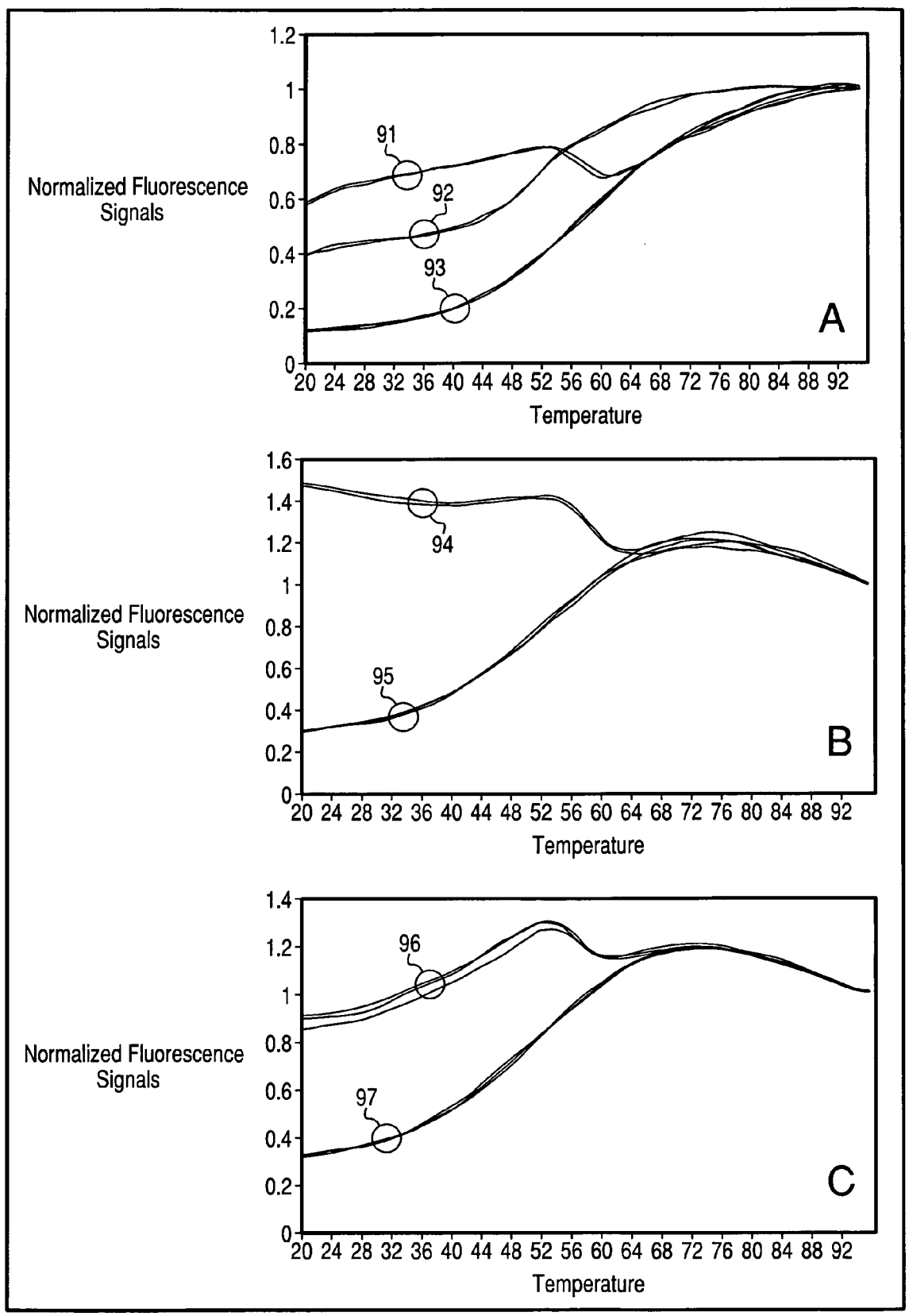
FIG. 9: EXO-R Probes using a BHQ1 on 5' terminus.

Example 5 (FIG. 9)

EXO-R Probes Using a BHQ1 on 5' Terminus

In this example we show that, (1) replacing the 5' fluorophore of an Exo-S probe with a 5' BHQ-1 quencher converts the Exo-S probe into an Exo-R probe that is no longer cleaved in a primer-independent manner by TAQ DNA polymerase, and (2) Exo-R probes bound to single-stranded DNA generated by LATE-PCR are not cleaved by TAQ DNA polymerase in a primer independent manner. FIG. 9 illustrates the results of this example. Panel A shows a melt profile of Exo-S probe probe/target hybrids in the absence (Lines 91) or presence (Lines 92) of TAQ DNA polymerase. This particular Exo-S probe consists of a 5' HEX fluorophore and a 3' BHQ-1 quencher. Lines 93 correspond to the background fluorescence signals of the no-template control samples. Reactions were carried out in a 25 μL volume and consisted of 1×PCR buffer (Invitrogen, Carlsbad, Calif.), 3 mM MgCl2, 150 nM synthetic target (see below), 500 nM Exo-S probe (see below) and, in the case of the samples with TAQ DNA polymerase, 1.25 units TAQ DNA polymerase (invitrogen, Carlsbad, Calif.). For the no-template control samples, TAQ DNA polymerase was included and the target sequence was replaced with 10 mM Tris-CI pH 8.3. Samples were incubated at 95° C. for 10 seconds and then at 20° C. for 20 minutes to allow formation of the Exo-S probe/target hybrids. Fluorescence signals were then collected as the sample temperature was raised from 20° C. to 95° C. at 1° C. intervals 90 seconds long each. For the samples without TAQ DNA polymerase (Lines 91), probe fluorescence signals match the probe fluorescence signals from the no-template controls above 65° C., a temperature range where the probe is completely melted off the target. In contrast, for samples with TAQ DNA polymerase, probe fluorescence signals above 65° C. are higher than the fluorescence signals from the no-template controls indicating probe cleavage and separation of the HEX fluorophore from the BHQ-1 quencher. This result demonstrates that Exo-S probes bound to synthetic targets are susceptible to cleavage by TAQ DNA polymerase in a primer-independent manner.
Sequences

```
Exo-S probe:

5' HEX AGCATACGGTTCAGTT 3' BHQ1
(SEQ ID NO: 22)

Synthetic Target:

5' AAGATCCTGAATAACTGAACCGTATGCTTGGCTAAAGTTC 3'
(SEQ ID NO: 23)

Underlined sequences correspond to the probe
target site.
```

The same probe sequence above was modified to have a 5' BHQ-1 quencher and 3' HEX fluorophore. The presence of a 5' BHQ-1 moiety turns the probe into a Exo-R probe that is resistant to cleavage by TAQ DNA polymerase in a primer-independent manner. Panel B shows a melt profile of such Exo-R probe-target hybrids in the presence of TAQ DNA polymerase (Lines 94). Lines 95 correspond to background fluorescence signals of probe-alone/no template control samples in the presence of TAQ DNA polymerase. Reaction conditions consisted of 1×PCR buffer (Invitrogen, Carlsbad, Calif.), 3 mM MgCl2, 150 nM synthetic target, 500 nM Exo-R probe (see below) and 1.25 units TAQ DNA polymerase (Invitrogen, Carlsbad, Calif.) in a final volume of 25 μl. For the no-template control samples, the target sequence was replaced with 10 nM Tris-Cl Ph 8.3. Samples were incubated at 20° C. for 20 minutes to allow formation of the Exo-R probe/target hybrids and then fluorescence signals were collected as the sample temperature was raised from 20° C. to 95° C. at 1° C. intervals 90 seconds long each. For the samples with Exo-R probe/target hybrids (Lines 94), fluorescence signals match the fluorescence signals from the no-template control above 65° C., a temperature range where the probe is completely melted off the target (Lines 95). This result demonstrates that, (1) Exo-R probes bound to synthetic targets are resistant to cleavage by TAQ DNA polymerase in a primer-independent manner, and (2) replacing the 5' HEX fluorophore with a 5' BHQ-1 quencher turns an Exo-S probe into an Exo-R probe.
Sequences

```
Exo-R probe:

5' BHQ-1 AGCATACGGTTTCAGTT 3' HEX
(SEQ ID NO: 22)

Synthetic Target: (same as above)

5' AAGATCCTGAATAACTGAACCGTATGCTTGGCTAAAGTTC 3'
(SEQ ID NO: 23)

Underlined sequences correspond to the probe
target site.
```

Panel C shows that the Exo-R probe described above is also resistant to cleavage by TAQ DNA polymerase when bound to single-stranded DNA generated by LATE-PCR. Single-stranded DNA products containing the target sequence for the Exo-R probe described above were generated via LATE-PCR in the presence of the Exo-R probe. At the end of amplification, the temperature was dropped to 20° C. and incubated for 20 min. to allow formation of the Exo-R/single-stranded amplicon hybrids. This figure shows a post-PCR melt curve analysis of Exo-R probe/single-stranded amplicon hybrids (Lines 96). Lines 97 correspond to background fluorescence signals of probe-alone/no template control samples. Similarly to Exo-R probe hybridized to synthetic targets (Panel B), complete melting of the Exo-R probe-amplicon hybrids above 65° C. results in background fluorescence signals equivalent to those of the no-template controls samples. This result demonstrates that Exo-R probes bound to targets generated by PCR are resistant to cleavage by TAQ DNA polymerase in a primer-independent manner. Reaction conditions for LATE-PCR amplification were 1×PCR buffer (Invitrogen, Carlsbad, Calif.), 3 mM MgCl$_2$, 250 nM dNTP mix (dATP, dGTP, dCTP, dTTP), 25 nM 9-22DD PrimeSafe, 500 nM 9-C3 PrimeSafe, 1.25 units TAQ DNA polymerase (Invitrogen, Carlsbad, Calif.), 50 nM limiting primer, 1 uM excess primer, 500 nM Exo-R probe, 1000 genome equivalents of human DNA (Corriell Cell Repository, Camden, N.J., catalog number; NA07348) in a final volume of 25 ul. The thermal cycle profile was 95° C. for 3 min, 70 cycles of 95° C. for 10 seconds, 64° C. for 10 seconds, and 72° C. for 20 seconds, then 20° C. for 20 minutes and a melt step with fluorescence acquisition from 20° C. to 95° C. at 1° C. intervals 90 seconds long each.

Sequences:

```
Limiting primer:

5' CCATTTCTTCCTCCTCCTCATAAGCATGGTACCTAT 3'
(SEQ ID NO: 24)

Excess primer:

5' CCCGCTGGTTCAATAATGTCTTTAA 3'
(SEQ ID NO: 25)

Exo-R probe (same as above)

5' BHQ-1 AGCATACGGTTCAGTT 3' HEX
(SEQ ID NO: 26)
```

Panel A—Example of an Exo-S probe tested on synthetic targets: This panel shows a melt curve analysis of Exo-S probe-target hybrids in the absence (Lines 91) or presence (Lines 92) of TAQ DNA polymerase. Lines 93 correspond to background fluorescence signals of probe-alone/no-template control samples in the presence of TAQ DNA polymerase. For the samples without TAQ DNA polymerase (Lines 91), complete melting of the probe-target hybrids above 65° C. results in background fluorescence signals equivalent to those of the no-template controls. For the samples with TAQ DNA polymerase, complete melting of the probe-target hybrids above 65° C. results in fluorescence signals that are higher that those of unbound probe due to probe cleavage and separation of the HEX fluorophore from the BHQ-1 quencher. This result demonstrates that Exo-S probes bound to synthetic are susceptible to cleavage by TAQ DNA polymerase in a primer-independent manner. Fluorescence signals were normalized at 95° C. to facilitate comparison of replicate samples.

Panel B: Example of an Exo-R probe tested on synthetic targets: This panel shows a melt curve analysis of Exo-R probe-target hybrids in the presence of TAQ DNA polymerase (Lines 94). Lines 95 correspond to background fluorescence signals of probe-alone/no-template control samples in the presence of TAQ DNA polymerase. Despite the presence of TAQ DNA polymerase, melting of the probe-target hybrids results in background fluorescence signals equivalent to those of the unbound probe. This result demonstrates that Exo-R probes bound to synthetic targets are resistant to cleavage by TAQ DNA polymerase in a primer-independent manner. Fluorescence signals were normalized at 95° C. to facilitate comparison of replicate samples.

Panel C: Example of an Exo-R probe tested on PCR products: The Exo-R probe described above is resistant to cleavage by TAQ DNA polymerase when bound to single-stranded DNA generated by LATE-PCR. Single-stranded DNA products containing the target sequence for the Exo-R probe described above were generated via LATE-PCR in the presence of the Exo-R probe. At the end of amplification, the temperature was dropped to 20° C. and incubated for 20 min. to allow formation of the Exo-R/amplicon hybrids. This figure shows a post-PCR melt curve analysis of Exo-R probe/amplicon hybrids (Lines 95). Lines 96 correspond to background fluorescence signals of probe-alone/no target samples. Similar to Exo-R probe hybridized to synthetic targets, melting of the Exo-R probe-amplicon hybrids results in background fluorescence signals equivalent to those of the no-template controls. This result demonstrates that Exo-R probes bound to targets generated by PCR are resistant to cleavage by TAQ DNA polymerase in a primer-independent manner. Fluorescence signals were normalized at 95° C. to facilitate comparison of replicate samples.

Figure 10:
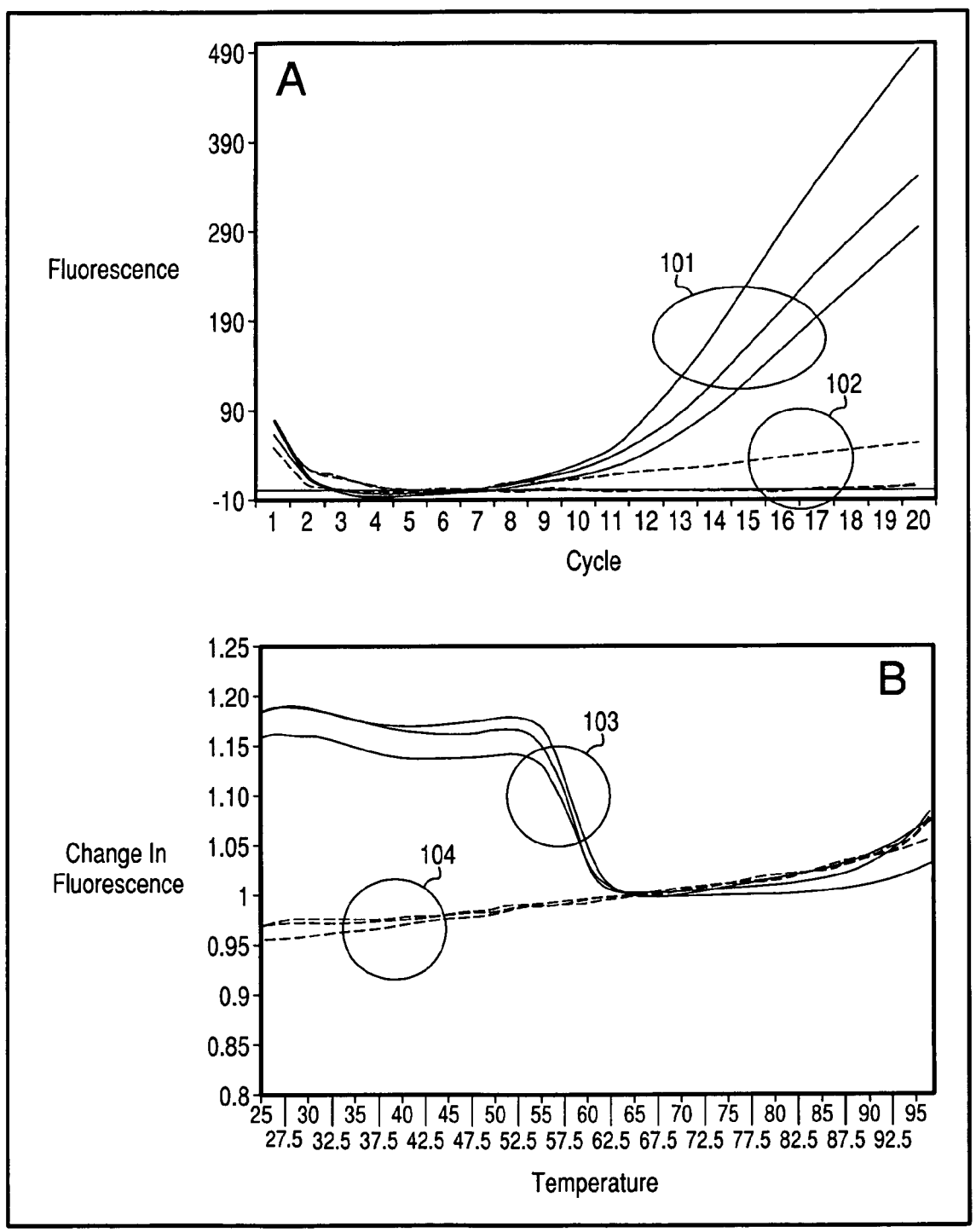
FIG. 10: EXO-R ROX probe to detect 7500 copies of a Newcastle DNA amplicon.

Example 6 (FIG. 10)

In this example, we show a LATE-PCR reaction using an EXO-R ROX probe to detect 7500 copies of a Newcastle DNA amplicon where there is no observed degradation of the ROX EXO-R probe during LATE-PCR amplification.

FIG. 10A shows both the LATE-PCR amplification of a 7500 copy Newcastle virus amplicon (lines 101) and the ROX EXO-R probe melt curves (solid lines) versus NTCs (lines 102). No probe degradation is observed in the melt curves FIG. 10B as all probe fluorescence (lines 103) and NTC fluorescence (lines 104) coincide when the probe is unbound at high temperature indicating that there is no free ROX fluorescence.

Sequences:

```
Limiting Primer:

5' GCATCAAATTCCCCACTGAGCCTC 3'      Tm: 67.9 C.
(SEQ ID NO: 26),

Excess Primer:

5' CCTGGTATTTATTCCTGTTTGAG 3'       Tm: 63.2 C.
(SEQ ID NO: 27),

Probe Sequence:

5' ROX-ATTTTGCGATATGATACCC-BHQ2 3'  Tm: 56 C.
(SEQ ID NO: 28),
```

| Stock Concentrations: | final conc. | volumes in 25 µL assay (µL) |
|---|---|---|
| 10x PCR Buffer | 1x | 2.5 µL |
| 10 mM dNTPs | 250 µM | 0.625 µL |
| 50 mM Mg$^{++}$ | 3 mM | 1.5 µL |
| 10 µM Limiting Primer | | 0.125 µL |
| 100 µM Excess Primer | | 0.250 µL |
| 10 µM Probes | 500 nM 2x | 1.25 µL |
| 10 µM C3-12B Primesafe | 300 nM | .750 µL |
| Total Mix: | | 8.25 µL |
| Pt TAQ (1.25 units): | | 0.25 |
| Water: | | 14.5 µL |
| DNA Amplicons | | 2.0 µL |
| (2 at 750, 7,500 copies/µL) | | |
| Total Volume: | | 25.0 µL |

Thermal Cycling Conditions:
　Stage 1: 95° C./3:00 minutes
　Stage 2: (95° C./0:10 secs—58°/62° C./0:15 secs—72° C./0:30 secs) Repeat 20 times
　Stage 3: (95° C./0:10 secs—58°/62° C./0:15 secs—72° C./0:30 secs—45° C./0:20 secs—25° C./0:20 secs) Repeat 20 times
　Stage 4: Hold 25° C./2:00 minutes
　Stage 5: Melt 25° C.-94° C.

Figure 11:
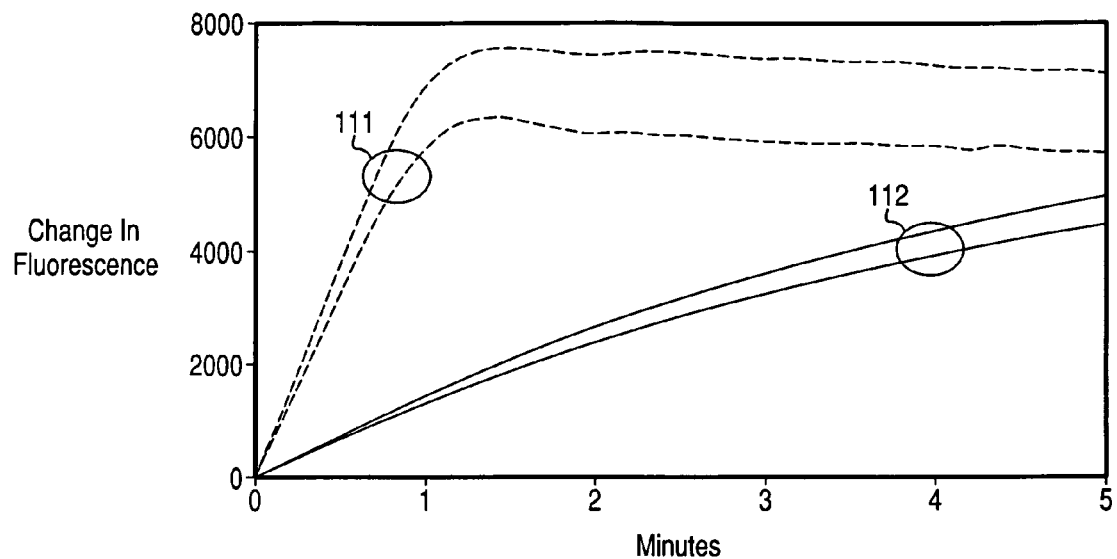
FIG. 11: Rate of Cleavage of an EXO-S Probe Under Isothermal vs Oscillating Conditions.

Example 7 (FIG. 11)

Rate of Cleavage of an EXO-S Probe Under Isothermal vs Oscillating Conditions

Comparing the rates of signal amplification under isothermal conditions 50° C. or oscillating between temperatures of 50° C. to 70° C. for 5 minutes. Both probe and complimentary target concentrations were 0.5 µM; the final reagent concentrations were 1× Invitrogen PCR buffer, 3 mM Mg$^{++}$, and 1.25 units of Invitrogen Taq polymerase. Lines (111) are replicates under oscillating conditions while lines (112) are replicates under isothermal conditions.

E9L Probe:

FAM 5' TTTCTAAATCCCATCAGACC 3'BHQ1
(SEQ ID NO: 29)

E9L Target with 12 base pair 3' and 5' overhangs:

3' ATATCTCGTGATAAAGATTTAGGGTAGTCTGGTATATGACTCA 5'
(SEQ ID NO: 30)

Figure 12:
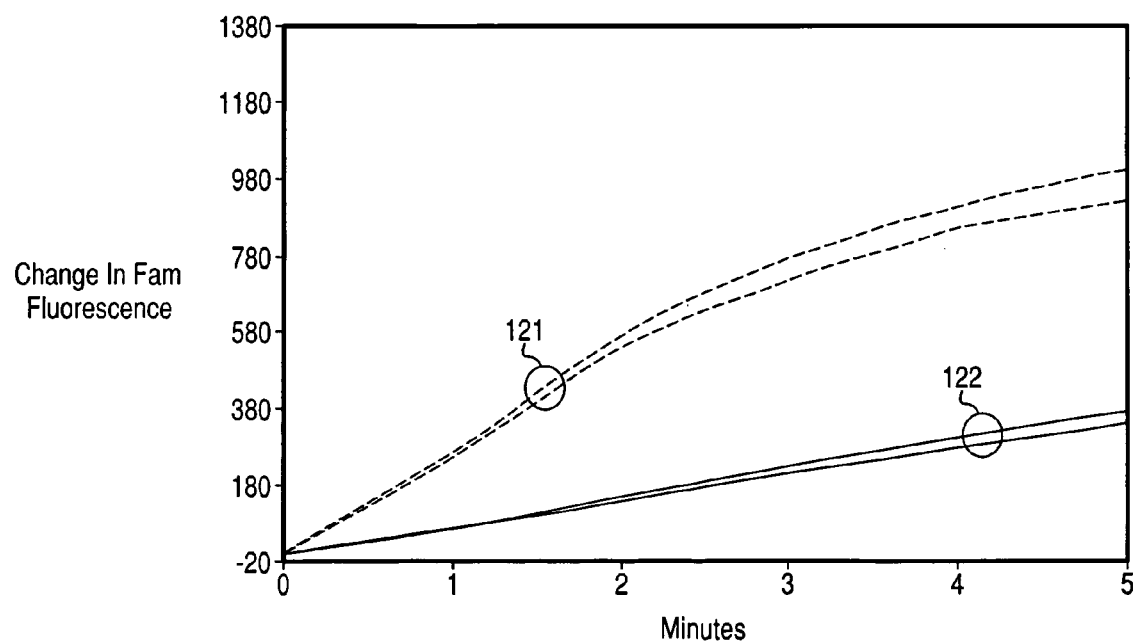
FIG. 12: The distance of an EXO-S probe to the 3' end of its complementary target affects the rate of cleavage.

Example 8 (FIG. 12)

The distance of an EXO-S probe to the 3' end of its complementary target affects the rate of cleavage.

The E9L probe was used at 0.2 uM while both targets were 0.05 uM; the final reagent concentrations were 1× Invitrogen PCR buffer, 3 mM Mg++, and 1.25 units of Invitrogen Taq polymerase. Lines (121) are replicates with 12 base pair 5' and 3' overhangs relative to the end of the probe-target hybrid complex. While lines (122) are replicates that have a 44 base pair 3' overhang relative to the 5'end of the probe-target hybrid complex.

E9L Probe:

FAM 5' TTTCTAAATCCCATCAGACC 3'BHQ1
(SEQ ID NO: 29)

E9L Target with 12 base pair 3' and 5' overhangs:

3' ATATCTCGTGATAAAGATTTAGGGTAGTCTGGTATATGACTCA 5'
(SEQ ID NO: 30)

E9L Target with 44 base pair 3' overhang:

3' ACCTACACGTTGAGAATCGGCTTCCCATACTCATATCTCGTGATAAG
TTTAGGGTAGTCTGG 5' (SEQ ID NO: 31)

Figure 13:
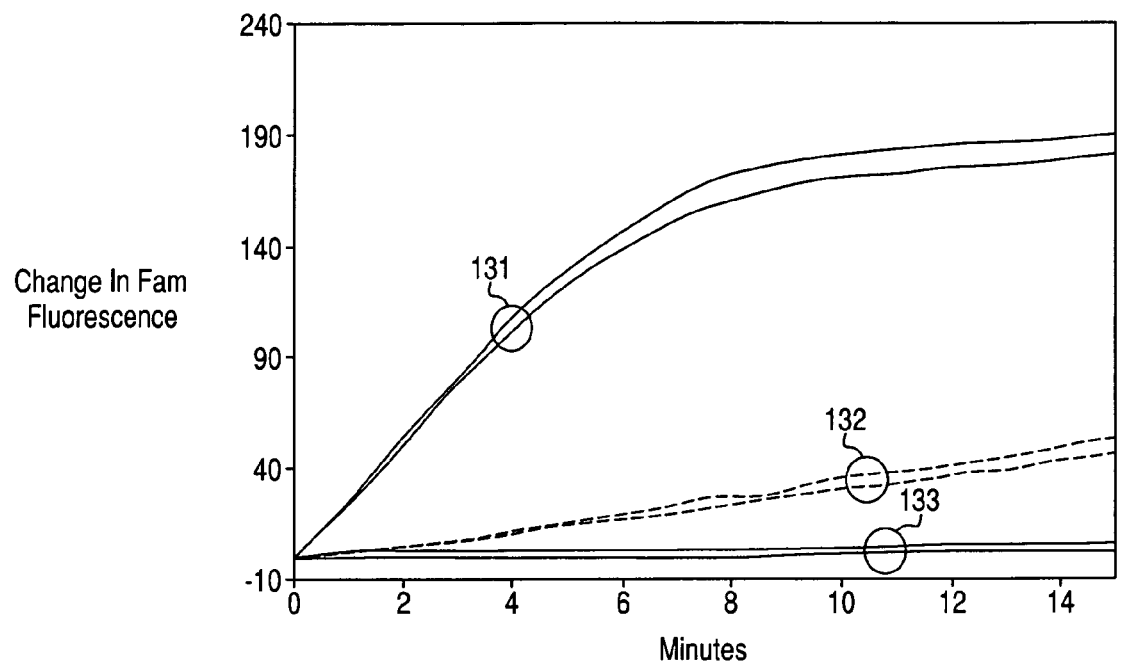
FIG. 13: Different rates of signal generation with single base pairing mismatches at the 5' end of the probe to the target during oscillation between 45° C. and 70° C. (Case 1).

Example 9 (FIG. 13)

Different rates of signal generation with single base pairing mismatches at the 5' end of the probe to the target during oscillation between 45° C. and 70° C. (Case 1).

The concentration of the probe is 0.2 µM rs498 with 0.05 µM targets; the final reagent concentrations were 1× Invitrogen PCR buffer, 3 mM Mg$^{++}$, and 1.25 units of Invitrogen Taq polymerase. and data collection at 70° C. Lines (131) are replicates that contain a mismatch A to A, lines (132) are replicates that are matched A to T. Lines (133) are replicates with the probe only.

rs498 probe:    FAM 5' AGACATGTTCCCTACT 3'BHQ1.
                (SEQ ID NO: 32)

(SEQ ID NO: 33)
CTTGAGTGGGAGGGTAGGGAACATGTCAGCCATAGGTTTC (SEQ ID NO: 34)
CTTGAGTGGGAGGGTAGGGAACATGTCTGCCATAGGTTTC

Figure 14:
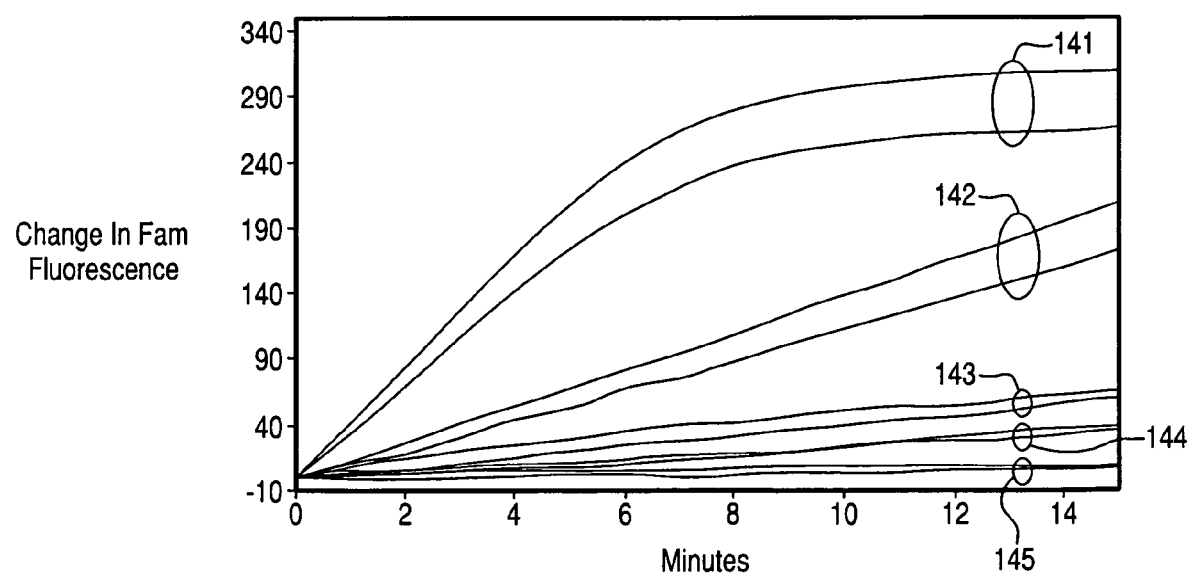
FIG. 14: Different rates of signal amplification with single base pairing mismatches at the 5' end of the probe to target during oscillation between 45° C. and 70° C. (Case 2).

Example 10 (FIG. 14)

Different rates of signal amplification with single base pairing mismatches at the 5' end of the probe to target during oscillation between 45° C. and 70° C. (Case 2).

The concentration of the probe is 0.2 µM rs498 with 0.05 µM targets, reagents were the same as above and data collection at 70° C. Lines (141) are replicates that contain a mismatch C to A, lines (142) are replicates that contain a mismatch C to T, lines (143) are replicates that contain a mismatch C to C, lines (144) are replicates that contain a matched C to G base pairing. While lines (145) are replicates with the probe only. The rs498 probe sequence is 5' FAM CGACATGTTCCCTACT BHQ 1 3' (SEQ ID NO: 35). The 5' C at the end of the probe sequence was mismatch (bold) to the 3' end of its complementary sequence (underlined) within the target strand:

(SEQ ID NO: 33)
5' CTTGAGTGGGAGGGTAGGGAACATGTCAGCCATAGGTTTC 3', (SEQ ID NO: 34)
5' CTTGAGTGGGAGGGTAGGGAACATGTCTGCCATAGGTTTC 3', (SEQ ID NO: 36)
5' CTTGAGTGGGAGGGTAGGGAACATGTCCGCCATAGGTTTC 3', or was matched (no-bold) to the 3' end of its complementary sequence (underlined) within the target strand.

(SEQ ID NO: 37)
5' CTTGAGTGGGAGGGTAGGGAACATGTCGGCCATAGGTTTC 3'.

Figure 15:
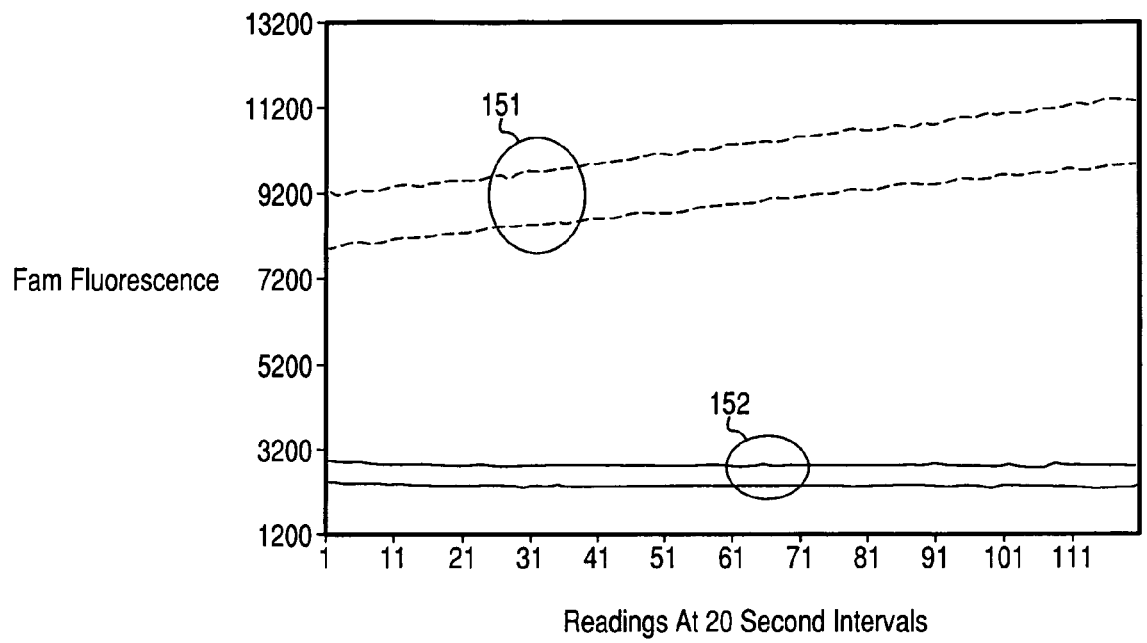
FIG. 15: Rate of signal amplification under isothermal conditions (50° C.) for 30 minutes.

Example 11 (FIG. 15)

Rate of signal amplification under isothermal conditions (50° C.) for 30 minutes. The FT probe was 0.5 µM and its complimentary target was 1.0 µM; the final reagent concentrations were 1× Invitrogen PCR buffer, 3 mM Mg++, and 1.25 units of Invitrogen Taq polymerase. Lines (151) are replicates of the FT probe and its complimentary target while lines (152) are the FT probe only. The sequence to the FT probe is 5'CCATGATACAAGCTTCC 3' (SEQ ID NO: 1) and the complementary sequence is 5' ACTTAGTAATTGG-GAAGCTTGTATCATGGCACTTAGAACCT3' (SEQ ID NO: 4)

Figure 16:
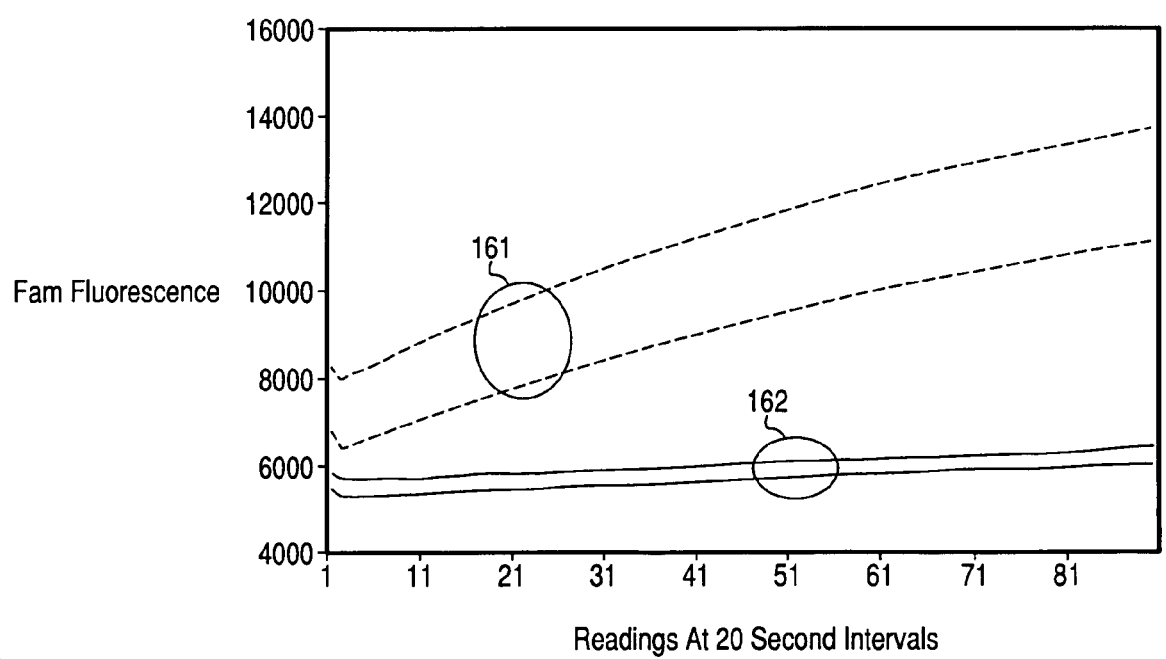
FIG. 16: Rate of signal amplification under oscillating conditions (45° C. to 70° C.).

Example 12 (FIG. 16)

Rate of signal amplification under oscillating conditions (45° C. to 70° C.). The FT probe was 0.5 µM and its complimentary target was 0.5 µM; the final reagent concentrations were 1× Invitrogen PCR buffer, 3 mM Mg++, and 1.25 units of Invitrogen Taq polymerase. Lines (161) are replicates of the FT probe and its complimentary target while lines (162) are the FT probe only. The sequence to the FT probe is 5' CCAT-GATACAAGCTTCC 3' (SEQ ID NO: 1 and the complimentary sequence is 5' ACTTAGTAATTGGGAAGCTTGTAT-CATGGCACTTAGAACCT 3' (SEQ ID NO: 4)

Figure 17:
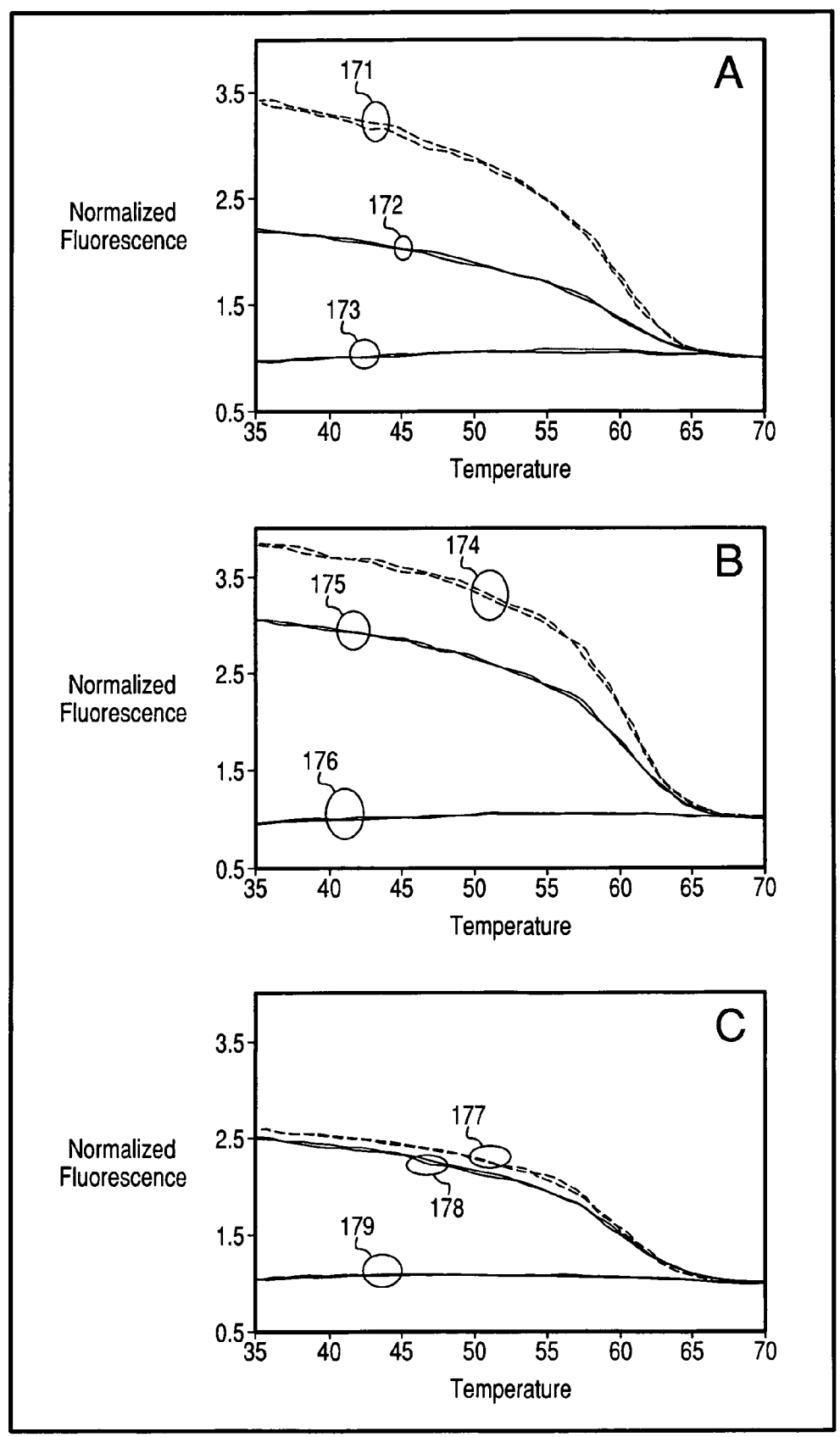
FIG. 17: Increasing the length of the 5' arm of a probe effects whether it is EXO-S or EXO-R probe.

Example 13 (FIG. 17)

Increasing the length of the 5' arm of a probe effects whether it is EXO-S or EXO-R probe. FIG. 17 A thru C shows a melt analysis done after 30 minutes of isothermal incubation of probe and its complimentary target at 50° C. with or without the presence of Taq polymerase. Samples that contain Taq and reach the same fluorescence values as those that do not contain Taq are indictive of EXO-R probe. All fluorescence values are normalized to 70° C. For FIG. 17A, the lines (171) are replicate samples of the FT probe (no modifications) target complex without Taq polymerase. Lines (172) are replicate samples that contain the FT probe and target with Taq polymerase. While lines (173) are the FT probe only. For FIG. 17B, lines (174) are replicate samples of the FT (1 bp) probe with single non-complementary base to target at the 5' end of probe in the presence of target without Taq polymerase. Lines (175) are replicate samples that contain the FT (1 bp) probe and target with Taq polymerase. While lines (176) are the FT (1 bp) probe only. For FIG. 17C, lines (177) are replicate samples of the FT (5 bp) probe with five non-complimentary bases to target at the 5' end of probe in the presence of target without Taq polymerase. Lines (178) are replicate samples that contain the FT (5 bp) probe and target with Taq polymerase. While lines (179) are the FT (5 bp) probe only.

The FT probe sequence was 5'CCATGATACAAGCTTCC 3' (SEQ ID NO: 1); the FT (1 bp) probe sequence was 5' ACCATGATACAAGCTTCC 3' (SEQ ID NO: 38); the FT (5 bp) probe was 5'TTTTTCCATGATACAAGCTTCC 3' (SEQ ID NO: 39). The FT target was 3'TCCAAGATTCAC GGTACTATGTTCGAAGGGTTAATGATTCA5' (SEQ ID NO: 40)

---

What is claimed is:

1. A non-symmetric polymerase chain reaction (PCR) amplification and detection method comprising
    (a) thermally cycling a reaction mixture through repeated thermal cycles that include a primer-annealing temperature, said reaction mixture containing a first deoxyribonucleic acid (DNA) amplification target sequence; a first excess primer and a first limiting primer; dNTPs; a thermostable DNA polymerase that is capable of extending said primers when they are hybridized to said target sequence but that does not exhibit target-independent-probe-cleavage; and a low-temperature, fluorophore-labeled first hybridization probe that signals upon hybridization to a first amplicon strand that is the extension product of the first excess primer, that has a concentration-adjusted melting temperature at least 5° C. below the concentration-adjusted melting temperature of the first limiting primer, and that is a linear DNA oligonucleotide whose susceptibility to primer-independent 5' exonuclease cleavage has been enhanced by a structural modification of said oligonucleotide;
    (b) hybridizing said first hybridization probe to said first amplicon strand at a first hybridization temperature after exhaustion of the limiting primer; and
    (c) detecting cleavage of said probe, wherein the structural modification of said first hybridization probe is selected from the group consisting of a 5' terminal nucleotide that is not complementary to the corresponding nucleotide of said first amplicon strand and a 5' terminal nucleotide having a label moiety linked to it by a chain comprised of at least three continuous methylene groups.

2. The method of claim 1, wherein detection includes rapid thermal oscillation around the melting temperature of said first hybridization probe.

3. The method of claim 1, wherein said chain is comprised of more than three contiguous methylene groups.

4. The method of claim 3, wherein said chain is comprised of six contiguous methylene groups.

5. The method of claim 1, wherein the reaction mixture contains a second DNA amplification target sequence, a second excess primer and a second limiting primer for said second DNA amplification target sequence, and a low-temperature, fluorophore-labeled second hybridization probe that signals upon hybridization to a second amplicon strand that is the extension product of the second excess primer, that has a concentration-adjusted melting temperature at least 5° C. below the concentration-adjusted melting temperature of the second limiting primer, wherein said second hybridization probe's concentration-adjusted melting temperature is at least 5° C. different from the concentration-adjusted melting temperature of said first hybridization probe; and wherein said method includes hybridizing said second hybridization probe to said second amplicon strand at a second hybridization temperature that is at least 5° C. different from said first hybridization temperature.

6. The method of claim 5, wherein said second probe is a linear DNA oligonucleotide whose susceptibility to primer-independent 5' exonuclease cleavage has been enhanced by a structural modification of said oligonucleotide, said structural modification being selected from the group consisting of a 5' terminal nucleotide that is not complementary to the corresponding nucleotide of said second amplicon strand and a 5' terminal nucleotide having a label moiety linked to it by a chain of at least three continuous methylene groups, and wherein said method includes detecting cleavage of said second hybridization probe.

7. The method of claim 6, wherein the concentration-adjusted melting temperature of said second probe is at least 10° C. below the concentration-adjusted melting temperature of said first probe and said second hybridization temperature is at least 10° C. below said first hybridization temperature.

8. The method of claim 6, wherein detection includes rapid thermal oscillation about the melting temperature of the second hybridization probe.

9. The method of claim 5, wherein said second probe is a linear DNA oligonucleotide made resistant to primer-independent 5' exonuclease cleavage by a structural modification selected from the group consisting of a 5' terminal arm composed of 2-7 nucleotides that do not hybridize to the second amplicon strand, a 5' terminal nucleotide having a quencher moiety linked to it other than by a chain of 3 or more contiguous methylene groups, and non-complimentary nucleotides at the 5' end of the probe that form a hairpin structure having a stem 2-5 nucleotides in length due to self-annealing at a temperature above 70° C.; and wherein said method includes detecting hybridization of said second probe.

10. The method of claim 9, wherein the concentration-adjusted melting temperature of said second probe is at least 10° C. above the concentration-adjusted melting temperature of said first probe and said second hybridization temperature is at least 10° C. above said first hybridization temperature.

11. The method of claim 9, wherein detection includes rapid thermal oscillation around the melting temperature of said first hybridization probe.

* * * * *

SEQUENCE LISTING

<160> NUMBER OF SEQ ID NOS: 40

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ccatgataca agcttcc                                                      17

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2 tttttccat gatacaagct tccttttt                                           29

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cggtgaaacc gcgcctgcaa tatacagc                                          28

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acttagtaat tgggaagctt gtatcatggc acttagaacc t                           41

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic

```
                                      oligonucleotide

<400> SEQUENCE: 5
aaaaaagctg tatattgcag gcgaaaaaa                                              29

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cactagggaa ctcgctg                                                           17

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
cgtttctcga ggtcctgcg                                                         19

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaggatagac cagctaccat gattgcc                                                27

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgttgtatga ccagagatct attttagtgt cct                                         33

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ataagtggag taaaattgga atcaatagg                                              29

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
ccatcagatt gaaaagaat tct                                         23

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcgttctga ctgaacagtg atcgag                                     26

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttctgactga acagctgatc gag                                        23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgactgaaca gctgatcgag                                            20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccctcttgaa attcccgaat gg                                         22

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcttgaaatt cccgaatgg                                             19

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```

```
ttgaaattcc cgaatgg                                                    17

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
cgctgaaagc gcgcctgcaa tttacagc                                        28

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaagtgtaa gattacaatg gcaggctcca ga                                   32

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttgcccaag ttttatcgtt cttctca                                         27

<210> SEQ ID NO 21
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
catgatacaa gcttc                                                      15

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
agcatacggt tcagtt                                                     16

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aagatcctga ataactgaac cgtatgcttg gctaaagttc                           40
```

```
<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccatttcttc ctcctcctca taagcatggt acctat                              36

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cccgctggtt caataatgtc tttaa                                          25

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcatcaaatt ccccactgag cctc                                           24

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cctggtattt attcctgttt gag                                            23

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
attttgcgat atgataccc                                                 19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
tttctaaatc ccatcagacc                                                20

<210> SEQ ID NO 30
```

```
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
actcagtata tggtctgatg ggatttagaa atagtgctct ata               43

<210> SEQ ID NO 31
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggtctgatgg gatttagaaa tagtgctcta tactcatacc cttcggctaa gagttgcaca    60
tcca                                                                 64

<210> SEQ ID NO 32
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
agacatgttc cctact                                             16

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cttgagtggg agggtaggga acatgtcagc cataggtttc                   40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cttgagtggg agggtaggga acatgtctgc cataggtttc                   40

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
cgacatgttc cctact                                             16

<210> SEQ ID NO 36
```

```
<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cttgagtggg agggtaggga acatgtccgc cataggtttc                              40

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cttgagtggg agggtaggga acatgtcggc cataggtttc                              40

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
accatgatac aagcttcc                                                      18

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
tttttccatg atacaagctt cc                                                 22

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
acttagtaat tgggaagctt gtatcatggc acttagaacc t                            41
```